US010265412B2

(12) United States Patent
Stern et al.

(10) Patent No.: US 10,265,412 B2
(45) Date of Patent: Apr. 23, 2019

(54) ENZYME REPLACEMENT THERAPY FOR TREATING LYSOSOMAL STORAGE DISEASES

(75) Inventors: Naftali Stern, Nir Zvi (IL); Ruth Navon, Ramat Gan (IL); Anthony Futerman, Rehovot (IL); Ari Zimran, Jerusalem (IL); Etty Osher, Rishon Le Zion (IL)

(73) Assignees: Ramot at Tel-Aviv University Ltd., Tel-Aviv (IL); Yeda Research and Development Co. Ltd. at the Weizmann Institute of Science, Rehovot (IL); The Medical Research, Infrastructure and Health Services Fund of the Tel Aviv Medical Center, Tel-Aviv (IL)

( * ) Notice: Subject to any disclaimer, the term of this patent is extended or adjusted under 35 U.S.C. 154(b) by 1553 days.

(21) Appl. No.: 12/278,378

(22) PCT Filed: Feb. 6, 2007

(86) PCT No.: PCT/IL2007/000152
§ 371 (c)(1),
(2), (4) Date: Dec. 29, 2008

(87) PCT Pub. No.: WO2007/091250
PCT Pub. Date: Aug. 16, 2007

(65) Prior Publication Data
US 2010/0183577 A1 Jul. 22, 2010

Related U.S. Application Data

(60) Provisional application No. 60/765,167, filed on Feb. 6, 2006.

(51) Int. Cl.
*A61K 38/47* (2006.01)
*A61K 38/19* (2006.01)
*A61K 47/64* (2017.01)
*C12N 9/24* (2006.01)
*C07K 14/535* (2006.01)

(52) U.S. Cl.
CPC ............ *A61K 47/642* (2017.08); *A61K 38/47* (2013.01); *C07K 14/535* (2013.01); *C12N 9/24* (2013.01); *C07K 2319/10* (2013.01)

(58) Field of Classification Search
CPC ............ C07K 14/535; C07K 2319/003; C07K 2319/06; C07K 2319/10
See application file for complete search history.

(56) References Cited

U.S. PATENT DOCUMENTS

| 6,027,720 A | 2/2000 | Kuga et al. .................. 424/85.1 |
| 6,518,235 B1 | 2/2003 | Oomura et al. .................. 514/2 |
| 6,555,660 B2 | 4/2003 | Nissen et al. ................. 530/397 |
| 6,831,158 B2 | 12/2004 | Nissen et al. ................. 530/397 |
| 2004/0101904 A1 | 5/2004 | Pardridge et al. ............. 435/7.1 |
| 2005/0142141 A1 | 6/2005 | Pardridge .................. 424/178.1 |

FOREIGN PATENT DOCUMENTS

| WO | WO 89/04663 | 6/1989 |
| WO | WO 89/10134 | 11/1989 |
| WO | WO 00/11173 | 3/2000 |
| WO | WO 03/057179 A2 | 7/2003 |
| WO | WO 2004/058287 | 7/2004 |

OTHER PUBLICATIONS

W. Pan et al. "Polypeptide Delivery Across the Blood Brain Barrier", Current Drug Targets, CNS Neurological Disorders 3:131-136 (2004).*
Guidotti, J.E. et al., "Retrovirus-Mediated Enzymatic Correction of Tay-Sachs Defect in Transduced and Non-Transduced Cells", Human Molecular Genetics, vol. 7, No. 5, pp. 831-838 (1998).
Lacorazza, H. Daniel et al., Expression of Human β-Hexosaminidase α-Subunit Gene (the Gene Defect of Tay-Sachs Disease) in Mouse Brains Upon Engraftment of Transduced Progenitor Cells, Nature Medicine, vol. 2, No. 4, pp. 424-429 (1996).
Mahuran, Don J., "Biochemical Consequences of Mutations Causing the GM2 Gangliosidoses", Biochimica et Biophysica Acta, vol. 1455, pp. 105-138 (1999).
Mahuran, Don J., "The Biochemistry of HEXA and HEXB Gene Mutations Causing $G_{m2}$ Gangliosidosis", Biochimica et Biophysica Acta, vol. 1096, pp. 87-94 (1991).
Miklyaeva, Elena I. et al., "Late Onset Tay-Sachs Disease in Mice with Targeted Disruption of the Hexa Gene: Behavioral Changes and Pathology of the Central Nervous System", Brain Research, vol. 1001, pp. 37-50 (2004).
Moos, Torben et al., "Restricted Transport of Anti-Transferrin Receptor Antibody (OX26) Through the Blood-Brain Barrier in the Rat", Journal of Neurochemistry, vol. 79, pp. 119-129 (2001).
Akli, S. et al., "Restoration of Hexosaminidase A Activity in Human Tay-Sachs Fibroblasts Via Adenoviral Vector-Mediated Gene Transfer", Gene Therapy, vol. 3, pp. 769-774 (1996).
Brady, Roscoe O. et al., "Enzyme-Replacement Therapy for Metabolic Storage Disorders", The Lancet Neurology, vol. 3, pp. 752-756 (2004).
Burguera, Bartolome et al., "The Long Form of the Leptin Receptor (OB-Rb) is Widely Expressed in the Human Brain", Neuroendocrinology, vol. 61, pp. 187-195 (2000).

(Continued)

*Primary Examiner* — Rebecca E Prouty
(74) *Attorney, Agent, or Firm* — Winston & Strawn LLP

(57) ABSTRACT

The present invention relates in general to the field of enzyme replacement therapy, and specifically to chimeric proteins including protein hormone-therapeutic protein conjugates and fusion proteins, wherein the protein hormone is selected from a protein hormone which is able to cross the blood brain barrier, for the treatment of lysosomal storage diseases, compositions of the same and to methods of use thereof.

16 Claims, 5 Drawing Sheets
Specification includes a Sequence Listing.

(56) References Cited

OTHER PUBLICATIONS

Conzelmann, E. et al., "Partial Enzyme Deficiencies: Residual Activities and the Development of Neurological Disorders", Dev. Neurosci., vol. 6, pp. 58-71 (1983/84).
Creighton, T. E. et al., "Protein: Structures and Molecular Properties", Peptide Synthesis, Chemical Nature of Polypeptides, pp. 55-60 (1984).
Dietz, Gunnar P.H. et al., "Delivery of Bioactive Molecules into the Cell: the Trojan Horse Approach", Mol. Cell. Neuroscience, vol. 27, pp. 85-131 (2004).
Myerowitz, Rachel et al., "Human β-Hexosaminidase α Chain: Coding Sequence and Homology with the β Chain", Proc. Natl. Acad. Science USA, vol. 82, pp. 7830-7834 (1985).
Ruth Navon, "Late-Onset $G_{m2}$ Gangliosidosis and Other Hexosaminidase Mutations Among Jews", Dept. of Human Genetics and Molecular Medicine and Laboratory of Molecular Genetics, pp. 185-197.
Neudorfer, Orit et al., "Late On-set Tay Sachs Disease: Phenotypic Characterization and Genotypic Correclations in 21 Affected Patients", Genetics in Medicine, vol. 7, No. 2 pp. 119-123 (2005).
Pardridge, William M., "Molecular Biology of the Blood-Brain Barrier", Molecular Biotechnology, vol. 30, pp. 57-69 (2005).
Paulson, Olaf B. et al., "Does the Release of Potassium from Astrocyte Endfeet Regulate Cerebral Blood Flow?", Science, vol. 237, pp. 896-898 (1987).
Pillai, Omathanu et al., "Polymers in Drug Delivery", Next Generation Therapeutics, pp. 447-451.
Schäbitz, W.R. et al., "Neuroprotective Effect of Granulocyte Colony-Stimulating Factor After Focal Cerebral Ischemia", Journal of the American Heart Association, pp. 745-751 (2003).
Wu, Dafang et al., "Drug Targeting of a Peptide Radiopharmaceutical through the Primate Blood-Brain Barrier In Vivo with a Monoclonal Antibody to the Human Insulin Receptor", The American Society for Clinical Investigation, Inc., vol. 100, No. 7, pp. 1804-1812 (1997).
Yamanaka, Shoh et al., "Targeted Disruption of the Hexa Gene Results in Mice with Biochemical and Pathologic Features of Tay-Sachs Disease", Proc. Natl. Acad. Science USA, vol. 91, pp. 9975-9979, (1994).
Zhang, Yun et al., "Delivery of β-Galactosidase to Mouse Brain Via the Blood-Brain Barrier Transferrin Receptor", The Journal of Pharmacology and Experimental Therapeutics, vol. 313, No. 3, pp. 1075-1081 (2005).

Sambrook et al., Molecular Cloning: A Laboratory Manual, Cold Springs Harbor Laboratory, New York, 1992.
International Search Report for PCT/IL2007/000152.
Dobrenis K. et al: XP008092925, "Enzyme Replacement in Cultured Neurons With Tetanus Toxin Fragment C TTC-Beta Hexosaminidase Ahexa Conjugate" Pediatric Research, vol. 23, No. 4, Part 2, p. 551A, 1988.
Dobrenis K. et al: XP008092927, "Enhanced Uptake of 1,2, Human Beta Hexosaminidase A Hex A by Coupling to Tetanus Toxin Fragment C TTC by Cns Neurons In-Vitro" Society for Neuroscience Abstracts, vol. 13, No. 3, p. 1685, 1987.
Rattazzi M.C. et al: XP008092993, "Enzyme Replacement 1,2, In GM2 Gangliosides 6-12,17,Pentamannosyl-6-Phosphate Beta Hexosaminidase A for Delivery to Cells Via The Mannose-6-Phosphate M6p Receptor" American Journal of Human Genetics, vol. 45, No. 4, Suppl, p. A10, 1989.
Rattazzi M.C. et al: XP008092994, "Enzyme Replacement Pentamannosyl-6-Phosphate Beta Hexosaminidase A PMP-Hex A for Delivery to Cells Via The Mannose-6-Phosphate M6p Receptor" Pediatric Research, vol. 27, No. 4, Part 2, p. 136A, 1990.
Beck M: XP008053810, "Enzymtherapie Bei lysosomalen speicherkrankheiten" Monatsschrift Fuer Kinderheilkunde,Springer Verlag, De, vol. 143, pp. 240-244, 1995.
Platt F M et al: XP002065772, "Prevention of Lysosomal Storage In Tay-Sachs Mice Treated With N-Butyldeoxynojirimycin", Science, Washington, DC, vol. 276, No. 5311, pp. 428-431, 1997.
Miklyaeva E. I. et al., Late Onset Tay-Sachs Disease In Mice With Targeted Disruption of The Hexa Gene: Behavioral Changes and Pathology of the Central Nervous System. Brain Research., vol. 1001 pp. 37-50, 2004.
Pennybacker M. et al.,"Identification of Domains in Human Beta-Hexosaminidase That Determine Substrate Specificity". The Journal of Biological Chemistry, vol. 271, No. 29, pp. 17377-17382, 1996.
Dobrenis K et al., (1992) Neuronal lysosomal enzyme replacement using fragment C of tetanus toxin. Proc Natl Acad Sci U S A 89(6): 2297-2301.
International Search Report PCT/IL2007/000152 dated Jul. 1, 2008.
Kostantin Dobrenis et al., "Neuronal Lysosomal Enzyme Replacement Using Fragment C of Tetanus Toxin", Proc. Nati. Acad. Sci. USA, vol. 89, pp. 2297-2301, (1992).
Weihong Pan et al., "Efficient Transfer of Receptor-Associated Protein (RAP) Across The Blood-Brain Barrier", Journal of Cell Science, vol.. 117 (21), pp. 5071-5078, (2004).

* cited by examiner

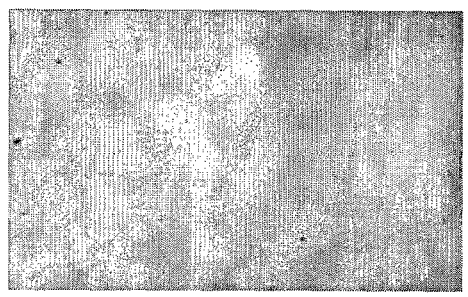
Figure 5A
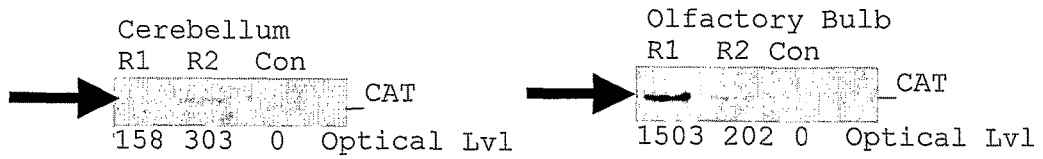
Figure 5B
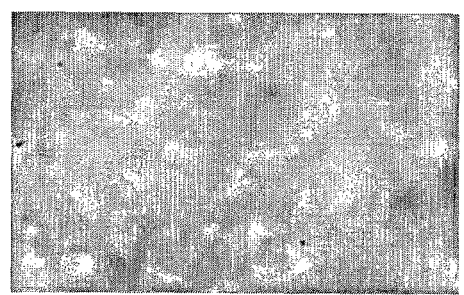
Figure 6A
Figure 6B
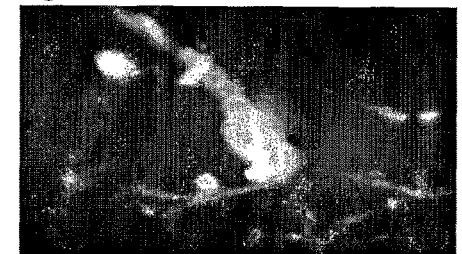
Figure 6C

SEQUENCE LISTING

```
<160> NUMBER OF SEQ ID NOS: 31

<210> SEQ ID NO 1
<211> LENGTH: 167
<212> TYPE: PRT
<213> ORGANISM: HOMO SAPIENS

<400> SEQUENCE: 1

Met His Trp Gly Thr Leu Cys Gly Phe Leu Trp Leu Trp Pro Tyr Leu
1               5                   10                  15

Phe Tyr Val Gln Ala Val Pro Ile Gln Lys Val Gln Asp Asp Thr Lys
            20                  25                  30

Thr Leu Ile Lys Thr Ile Val Thr Arg Ile Asn Asp Ile Ser His Thr
        35                  40                  45

Gln Ser Val Ser Ser Lys Gln Lys Val Thr Gly Leu Asp Phe Ile Pro
```

```
                    50                  55                  60
Gly Leu His Pro Ile Leu Thr Leu Ser Lys Met Asp Gln Thr Leu Ala
 65                  70                  75                  80

Val Tyr Gln Gln Ile Leu Thr Ser Met Pro Ser Arg Asn Val Ile Gln
                 85                  90                  95

Ile Ser Asn Asp Leu Glu Asn Leu Arg Asp Leu His Val Leu Ala
            100                 105                 110

Phe Ser Lys Ser Cys His Leu Pro Trp Ala Ser Gly Leu Glu Thr Leu
            115                 120                 125

Asp Ser Leu Gly Gly Val Leu Glu Ala Ser Gly Tyr Ser Thr Glu Val
        130                 135                 140

Val Ala Leu Ser Arg Leu Gln Gly Ser Leu Gln Asp Met Leu Trp Gln
145                 150                 155                 160

Leu Asp Leu Ser Pro Gly Cys
                165
```

<210> SEQ ID NO 2
<211> LENGTH: 147
<212> TYPE: PRT
<213> ORGANISM: HOMO SAPIENS

<400> SEQUENCE: 2

```
Met Val Pro Ile Gln Lys Val Gln Asp Asp Thr Lys Thr Leu Ile Lys
 1               5                  10                  15

Thr Ile Val Thr Arg Ile Asn Asp Ile Ser His Thr Gln Ser Val Ser
                20                  25                  30

Ser Lys Gln Lys Val Thr Gly Leu Asp Phe Ile Pro Gly Leu His Pro
            35                  40                  45

Ile Leu Thr Leu Ser Lys Met Asp Gln Thr Leu Ala Val Tyr Gln Gln
         50                 55                  60

Ile Leu Thr Ser Met Pro Ser Arg Asn Val Ile Gln Ile Ser Asn Asp
 65                 70                  75                  80

Leu Glu Asn Leu Arg Asp Leu His Val Leu Ala Phe Ser Lys Ser
                85                  90                  95

Cys His Leu Pro Trp Ala Ser Gly Leu Glu Thr Leu Asp Ser Leu Gly
            100                 105                 110

Gly Val Leu Glu Ala Ser Gly Tyr Ser Thr Glu Val Val Ala Leu Ser
        115                 120                 125

Arg Leu Gln Gly Ser Leu Gln Asp Met Leu Trp Gln Leu Asp Leu Ser
    130                 135                 140

Pro Gly Cys
145
```

<210> SEQ ID NO 3
<211> LENGTH: 501
<212> TYPE: DNA
<213> ORGANISM: HOMO SAPIENS

<400> SEQUENCE: 3

```
atgcattggg gaaccctgtg cggattcttg tggctttggc cctatctttt ctatgtccaa      60
gctgtgccca tccaaaaagt ccaagatgac accaaaaccc tcatcaagac aattgtcacc     120
aggatcaatg acatttcaca cacgcagtca gtctcctcca acagaaagt caccggtttg      180 gacttcattc ctgggctcca ccccatcctg accttatcca gatggaccac agactggca     240 gtctaccaac agatcctcac cagtatgcct tccagaaacg tgatccaaat atccaacgac     300
```

```
ctggagaacc tccgggatct tcttcacgtg ctggccttct ctaagagctg ccacttgccc    360
tgggccagtg gcctggagac cttggacagc ctggggggtg tcctggaagc ttcaggctac    420
tccacagagg tggtggccct gagcaggctg cagggggtctc tgcaggacat gctgtggcag    480
ctggacctca gccctgggtg c                                              501

<210> SEQ ID NO 4
<211> LENGTH: 441
<212> TYPE: DNA
<213> ORGANISM: HOMO SAPIENS

<400> SEQUENCE: 4
atggtgccca tccaaaaagt ccaagatgac accaaaaccc tcatcaagac aattgtcacc     60
aggatcaatg acatttcaca cacgcagtca gtctcctcca aacagaaagt caccggtttg    120
gacttcattc ctgggctcca ccccatcctg accttatcca agatggacca gacactggca    180
gtctaccaac agatcctcac cagtatgcct tccagaaacg tgatccaaat atccaacgac    240
ctggagaacc tccgggatct tcttcacgtg ctggccttct ctaagagctg ccacttgccc    300
tgggccagtg gcctggagac cttggacagc ctggggggtg tcctggaagc ttcaggctac    360
tccacagagg tggtggccct gagcaggctg cagggggtctc tgcaggacat gctgtggcag    420
ctggacctca gccctgggtg c                                              441

<210> SEQ ID NO 5
<211> LENGTH: 207
<212> TYPE: PRT
<213> ORGANISM: HOMO SAPIENS

<400> SEQUENCE: 5

Met Ala Gly Pro Ala Thr Gln Ser Pro Met Lys Leu Met Ala Leu Gln
1               5                   10                  15

Leu Leu Leu Trp His Ser Ala Leu Trp Thr Val Gln Glu Ala Thr Pro
            20                  25                  30

Leu Gly Pro Ala Ser Ser Leu Pro Gln Ser Phe Leu Leu Lys Cys Leu
        35                  40                  45

Glu Gln Val Arg Lys Ile Gln Gly Asp Gly Ala Ala Leu Gln Glu Lys
    50                  55                  60

Leu Val Ser Glu Cys Ala Thr Tyr Lys Leu Cys His Pro Glu Glu Leu
65                  70                  75                  80

Val Leu Leu Gly His Ser Leu Gly Ile Pro Trp Ala Pro Leu Ser Ser
                85                  90                  95

Cys Pro Ser Gln Ala Leu Gln Leu Ala Gly Cys Leu Ser Gln Leu His
            100                 105                 110

Ser Gly Leu Phe Leu Tyr Gln Gly Leu Leu Gln Ala Leu Glu Gly Ile
        115                 120                 125

Ser Pro Glu Leu Gly Pro Thr Leu Asp Thr Leu Gln Leu Asp Val Ala
    130                 135                 140

Asp Phe Ala Thr Thr Ile Trp Gln Gln Met Glu Glu Leu Gly Met Ala
145                 150                 155                 160

Pro Ala Leu Gln Pro Thr Gln Gly Ala Met Pro Ala Phe Ala Ser Ala
                165                 170                 175

Phe Gln Arg Arg Ala Gly Gly Val Leu Val Ala Ser His Leu Gln Ser
            180                 185                 190

Phe Leu Glu Val Ser Tyr Arg Val Leu Arg His Leu Ala Gln Pro
        195                 200                 205
```

<210> SEQ ID NO 6
<211> LENGTH: 177
<212> TYPE: PRT
<213> ORGANISM: HOMO SAPIENS

<400> SEQUENCE: 6

Thr Pro Leu Gly Pro Ala Ser Ser Leu Pro Gln Ser Phe Leu Leu Lys
1               5                   10                  15

Cys Leu Glu Gln Val Arg Lys Ile Gln Gly Asp Gly Ala Ala Leu Gln
            20                  25                  30

Glu Lys Leu Val Ser Glu Cys Ala Thr Tyr Lys Leu Cys His Pro Glu
        35                  40                  45

Glu Leu Val Leu Leu Gly His Ser Leu Gly Ile Pro Trp Ala Pro Leu
    50                  55                  60

Ser Ser Cys Pro Ser Gln Ala Leu Gln Leu Ala Gly Cys Leu Ser Gln
65                  70                  75                  80

Leu His Ser Gly Leu Phe Leu Tyr Gln Gly Leu Leu Gln Ala Leu Glu
                85                  90                  95

Gly Ile Ser Pro Glu Leu Gly Pro Thr Leu Asp Thr Leu Gln Leu Asp
            100                 105                 110

Val Ala Asp Phe Ala Thr Thr Ile Trp Gln Gln Met Glu Glu Leu Gly
        115                 120                 125

Met Ala Pro Ala Leu Gln Pro Thr Gln Gly Ala Met Pro Ala Phe Ala
    130                 135                 140

Ser Ala Phe Gln Arg Arg Ala Gly Gly Val Leu Val Ala Ser His Leu
145                 150                 155                 160

Gln Ser Phe Leu Glu Val Ser Tyr Arg Val Leu Arg His Leu Ala Gln
                165                 170                 175

Pro

<210> SEQ ID NO 7
<211> LENGTH: 624
<212> TYPE: DNA
<213> ORGANISM: HOMO SAPIENS

<400> SEQUENCE: 7
atggctggac ctgccaccca gagccccatg aagctgatgg ccctgcagct gctgctgtgg    60
cacagtgcac tctggacagt gcaggaagcc acccccctgg gccctgccag ctccctgccc   120
cagagcttcc tgctcaagtg cttagagcaa gtgaggaaga tccagggcga tggcgcagcg   180
ctccaggaga agctggtgag tgagtgtgcc acctacaagc tgtgccaccc cgaggagctg   240
gtgctgctcg gacactctct gggcatcccc tgggctcccc tgagcagctg ccccagccag   300
gccctgcagc tggcaggctg cttgagccaa ctccatagcg gcctttttcct ctaccagggg   360 ctcctgcagg ccctggaagg gatctccccc gagttgggtc ccaccttgga cacactgcag   420
ctggacgtcg ccgactttgc caccaccatc tggcagcaga tggaagaact gggaatggcc   480
cctgccctgc agcccaccca gggtgccatg ccggccttcg cctctgcttt ccagcgccgg   540
gcaggagggg tcctggttgc ctcccatctg cagagcttcc tggaggtgtc gtaccgcgtt   600
ctacgccacc ttgcccagcc ctga                                          624

<210> SEQ ID NO 8
<211> LENGTH: 534
<212> TYPE: DNA
<213> ORGANISM: HOMO SAPIENS

<400> SEQUENCE: 8

```
acccccctgg gccctgccag ctccctgccc cagagcttcc tgctcaagtg cttagagcaa      60
gtgaggaaga tccagggcga tggcgcagcg ctccaggaga agctggtgag tgagtgtgcc     120
acctacaagc tgtgccaccc cgaggagctg gtgctgctcg acactctct gggcatcccc      180
tgggctcccc tgagcagctg cccagccag gccctgcagc tggcaggctg cttgagccaa     240
ctccatagcg gccttttcct ctaccagggg ctcctgcagg ccctggaagg gatcccccc     300
gagttgggtc ccaccttgga cacactgcag ctggacgtcg ccgactttgc caccaccatc     360
tggcagcaga tggaagaact gggaatggcc cctgccctgc agcccaccca gggtgccatg     420
ccggccttcg cctctgcttt ccagcgccgg gcaggagggg tcctggttgc ctcccatctg     480
cagagcttcc tggaggtgtc gtaccgcgtt ctacgccacc ttgcccagcc ctga           534
```

<210> SEQ ID NO 9
<211> LENGTH: 204
<212> TYPE: PRT
<213> ORGANISM: HOMO SAPIENS

<400> SEQUENCE: 9

```
Met Ala Gly Pro Ala Thr Gln Ser Pro Met Lys Leu Met Ala Leu Gln
  1               5                  10                  15

Leu Leu Leu Trp His Ser Ala Leu Trp Thr Val Gln Glu Ala Thr Pro
             20                  25                  30

Leu Gly Pro Ala Ser Ser Leu Pro Gln Ser Phe Leu Leu Lys Cys Leu
         35                  40                  45

Glu Gln Val Arg Lys Ile Gln Gly Asp Gly Ala Ala Leu Gln Glu Lys
     50                  55                  60

Leu Cys Ala Thr Tyr Lys Leu Cys His Pro Glu Glu Leu Val Leu Leu
 65                  70                  75                  80

Gly His Ser Leu Gly Ile Pro Trp Ala Pro Leu Ser Ser Cys Pro Ser
                 85                  90                  95

Gln Ala Leu Gln Leu Ala Gly Cys Leu Ser Gln Leu His Ser Gly Leu
            100                 105                 110

Phe Leu Tyr Gln Gly Leu Leu Gln Ala Leu Glu Gly Ile Ser Pro Glu
        115                 120                 125

Leu Gly Pro Thr Leu Asp Thr Leu Gln Leu Asp Val Ala Asp Phe Ala
    130                 135                 140

Thr Thr Ile Trp Gln Gln Met Glu Glu Leu Gly Met Ala Pro Ala Leu
145                 150                 155                 160

Gln Pro Thr Gln Gly Ala Met Pro Ala Phe Ala Ser Ala Phe Gln Arg
                165                 170                 175

Arg Ala Gly Gly Val Leu Val Ala Ser His Leu Gln Ser Phe Leu Glu
            180                 185                 190

Val Ser Tyr Arg Val Leu Arg His Leu Ala Gln Pro
        195                 200
```

<210> SEQ ID NO 10
<211> LENGTH: 174
<212> TYPE: PRT
<213> ORGANISM: HOMO SAPIENS

<400> SEQUENCE: 10

```
Thr Pro Leu Gly Pro Ala Ser Ser Leu Pro Gln Ser Phe Leu Leu Lys
  1               5                  10                  15

Cys Leu Glu Gln Val Arg Lys Ile Gln Gly Asp Gly Ala Ala Leu Gln
```

```
                    20                  25                  30
Glu Lys Leu Cys Ala Thr Tyr Lys Leu Cys His Pro Glu Glu Leu Val
                35                  40                  45

Leu Leu Gly His Ser Leu Gly Ile Pro Trp Ala Pro Leu Ser Ser Cys
        50                  55                  60

Pro Ser Gln Ala Leu Gln Leu Ala Gly Cys Leu Ser Gln Leu His Ser
65                  70                  75                  80

Gly Leu Phe Leu Tyr Gln Gly Leu Leu Gln Ala Leu Glu Gly Ile Ser
                85                  90                  95

Pro Glu Leu Gly Pro Thr Leu Asp Thr Leu Gln Leu Asp Val Ala Asp
            100                 105                 110

Phe Ala Thr Thr Ile Trp Gln Gln Met Glu Glu Leu Gly Met Ala Pro
            115                 120                 125

Ala Leu Gln Pro Thr Gln Gly Ala Met Pro Ala Phe Ala Ser Ala Phe
        130                 135                 140

Gln Arg Arg Ala Gly Gly Val Leu Val Ala Ser His Leu Gln Ser Phe
145                 150                 155                 160

Leu Glu Val Ser Tyr Arg Val Leu Arg His Leu Ala Gln Pro
                165                 170

<210> SEQ ID NO 11
<211> LENGTH: 615
<212> TYPE: DNA
<213> ORGANISM: HOMO SAPIENS

<400> SEQUENCE: 11
atggctggac ctgccaccca gagccccatg aagctgatgg ccctgcagct gctgctgtgg      60
cacagtgcac tctggacagt gcaggaagcc accccctgg gccctgccag ctccctgccc     120
cagagcttcc tgctcaagtg cttagagcaa gtgaggaaga tccagggcga tggcgcagcg     180
ctccaggaga agctgtgtgc cacctacaag ctgtgccacc cgaggagct ggtgctgctc     240 ggacactctc tgggcatccc ctgggctccc ctgagcagct gccccagcca ggccctgcag     300
ctggcaggct gcttgagcca actccatagc ggcctttccc tctaccaggg gctcctgcag     360
gccctggaag ggatctcccc cgagttgggt cccaccttgg acacactgca gctggacgtc     420
gccgactttg ccaccaccat ctggcagcag atggaagaac tgggaatggc ccctgccctg     480
cagcccaccc agggtgccat gccggccttc gcctctgctt tccagcgccg ggcaggaggg     540
gtcctagttg cctcccatct gcagagcttc ctggaggtgt cgtaccgcgt tctacgccac     600
cttgcccagc cctga                                                      615

<210> SEQ ID NO 12
<211> LENGTH: 535
<212> TYPE: DNA
<213> ORGANISM: HOMO SAPIENS

<400> SEQUENCE: 12
gcaggaagcc accccctgg gccctgccag ctccctgccc cagagcttcc tgctcaagtg       60
cttagagcaa gtgaggaaga tccagggcga tggcgcagcg ctccaggaga agctgtgtgc     120
cacctacaag ctgtgccacc cgaggagct ggtgctgctc ggacactctc tgggcatccc     180
ctgggctccc ctgagcagct gccccagcca ggccctgcag ctggcaggct gcttgagcca     240
actccatagc ggcctttccc tctaccaggg gctcctgcag gccctggaag ggatctcccc     300
cgagttgggt cccaccttgg acacactgca gctggacgtc gccgactttg ccaccaccat     360
```

```
ctggcagcag atggaagaac tgggaatggc ccctgccctg cagcccaccc agggtgccat    420
gccggccttc gcctctgctt ccagcgccg  ggcaggaggg gtcctagttg cctcccatct    480
gcagagcttc ctggaggtgt cgtaccgcgt tctacgccac cttgcccagc cctga         535
```

<210> SEQ ID NO 13
<211> LENGTH: 529
<212> TYPE: PRT
<213> ORGANISM: HOMO SAPIENS

<400> SEQUENCE: 13

```
Met Thr Ser Ser Arg Leu Trp Phe Ser Leu Leu Ala Ala Ala Phe
1               5                   10                  15

Ala Gly Arg Ala Thr Ala Leu Trp Pro Trp Pro Gln Asn Phe Gln Thr
            20                  25                  30

Ser Asp Gln Arg Tyr Val Leu Tyr Pro Asn Asn Phe Gln Phe Gln Tyr
        35                  40                  45

Asp Val Ser Ser Ala Ala Gln Pro Gly Cys Ser Val Leu Asp Glu Ala
    50                  55                  60

Phe Gln Arg Tyr Arg Asp Leu Leu Phe Gly Ser Gly Ser Trp Pro Arg
65                  70                  75                  80

Pro Tyr Leu Thr Gly Lys Arg His Thr Leu Glu Lys Asn Val Leu Val
                85                  90                  95

Val Ser Val Val Thr Pro Gly Cys Asn Gln Leu Pro Thr Leu Glu Ser
            100                 105                 110

Val Glu Asn Tyr Thr Leu Thr Ile Asn Asp Asp Gln Cys Leu Leu Leu
        115                 120                 125

Ser Glu Thr Val Trp Gly Ala Leu Arg Gly Leu Glu Thr Phe Ser Gln
    130                 135                 140

Leu Val Trp Lys Ser Ala Glu Gly Thr Phe Phe Ile Asn Lys Thr Glu
145                 150                 155                 160

Ile Glu Asp Phe Pro Arg Phe Pro His Arg Gly Leu Leu Leu Asp Thr
                165                 170                 175

Ser Arg His Tyr Leu Pro Leu Ser Ser Ile Leu Asp Thr Leu Asp Val
            180                 185                 190

Met Ala Tyr Asn Lys Leu Asn Val Phe His Trp His Leu Val Asp Asp
        195                 200                 205

Pro Ser Phe Pro Tyr Glu Ser Phe Thr Phe Pro Glu Leu Met Arg Lys
    210                 215                 220

Gly Ser Tyr Asn Pro Val Thr His Ile Tyr Thr Ala Gln Asp Val Lys
225                 230                 235                 240

Glu Val Ile Glu Tyr Ala Arg Leu Arg Gly Ile Arg Val Leu Ala Glu
                245                 250                 255

Phe Asp Thr Pro Gly His Thr Leu Ser Trp Gly Pro Gly Ile Pro Gly
            260                 265                 270

Leu Leu Thr Pro Cys Tyr Ser Gly Ser Glu Pro Ser Gly Thr Phe Gly
        275                 280                 285

Pro Val Asn Pro Ser Leu Asn Asn Thr Tyr Glu Phe Met Ser Thr Phe
    290                 295                 300

Phe Leu Glu Val Ser Ser Val Phe Pro Asp Phe Tyr Leu His Leu Gly
305                 310                 315                 320

Gly Asp Glu Val Asp Phe Thr Cys Trp Lys Ser Asn Pro Glu Ile Gln
                325                 330                 335

Asp Phe Met Arg Lys Lys Gly Phe Gly Glu Asp Phe Lys Gln Leu Glu
            340                 345                 350
```

-continued

```
Ser Phe Tyr Ile Gln Thr Leu Leu Asp Ile Val Ser Ser Tyr Gly Lys
    355                 360                 365
Gly Tyr Val Val Trp Gln Glu Val Phe Asp Asn Lys Val Lys Ile Gln
    370                 375                 380
Pro Asp Thr Ile Ile Gln Val Trp Arg Glu Asp Ile Pro Val Asn Tyr
385                 390                 395                 400
Met Lys Glu Leu Glu Leu Val Thr Lys Ala Gly Phe Arg Ala Leu Leu
                405                 410                 415
Ser Ala Pro Trp Tyr Leu Asn Arg Ile Ser Tyr Gly Pro Asp Trp Lys
                420                 425                 430
Asp Phe Tyr Val Val Glu Pro Leu Ala Phe Glu Gly Thr Pro Glu Gln
                435                 440                 445
Lys Ala Leu Val Ile Gly Gly Glu Ala Cys Met Trp Gly Glu Tyr Val
                450                 455                 460
Asp Asn Thr Asn Leu Val Pro Arg Leu Trp Pro Arg Ala Gly Ala Val
465                 470                 475                 480
Ala Glu Arg Leu Trp Ser Asn Lys Leu Thr Ser Asp Leu Thr Phe Ala
                485                 490                 495
Tyr Glu Arg Leu Ser His Phe Arg Cys Glu Leu Leu Arg Arg Gly Val
                500                 505                 510
Gln Ala Gln Pro Leu Asn Val Gly Phe Cys Glu Gln Glu Phe Glu Gln
                515                 520                 525
Thr
```

<210> SEQ ID NO 14
<211> LENGTH: 421
<212> TYPE: PRT
<213> ORGANISM: HOMO SAPIENS

<400> SEQUENCE: 14

```
Thr Leu Glu Ser Val Glu Asn Tyr Thr Leu Thr Ile Asn Asp Asp Gln
1               5                   10                  15
Cys Leu Leu Leu Ser Glu Thr Val Trp Gly Ala Leu Arg Gly Leu Glu
                20                  25                  30
Thr Phe Ser Gln Leu Val Trp Lys Ser Ala Glu Gly Thr Phe Phe Ile
            35                  40                  45
Asn Lys Thr Glu Ile Glu Asp Phe Pro Arg Phe Pro His Arg Gly Leu
    50                  55                  60
Leu Leu Asp Thr Ser Arg His Tyr Leu Pro Leu Ser Ser Ile Leu Asp
65                  70                  75                  80
Thr Leu Asp Val Met Ala Tyr Asn Lys Leu Asn Val Phe His Trp His
                85                  90                  95
Leu Val Asp Asp Pro Ser Phe Pro Tyr Glu Ser Phe Thr Phe Pro Glu
                100                 105                 110
Leu Met Arg Lys Gly Ser Tyr Asn Pro Val Thr His Ile Tyr Thr Ala
                115                 120                 125
Gln Asp Val Lys Glu Val Ile Glu Tyr Ala Arg Leu Arg Gly Ile Arg
                130                 135                 140
Val Leu Ala Glu Phe Asp Thr Pro Gly His Thr Leu Ser Trp Gly Pro
145                 150                 155                 160
Gly Ile Pro Gly Leu Leu Thr Pro Cys Tyr Ser Gly Ser Glu Pro Ser
                165                 170                 175
Gly Thr Phe Gly Pro Val Asn Pro Ser Leu Asn Asn Thr Tyr Glu Phe
                180                 185                 190
```

```
Met Ser Thr Phe Phe Leu Glu Val Ser Val Phe Pro Asp Phe Tyr
            195                 200                 205

Leu His Leu Gly Gly Asp Glu Val Asp Phe Thr Cys Trp Lys Ser Asn
            210                 215                 220

Pro Glu Ile Gln Asp Phe Met Arg Lys Lys Gly Phe Gly Glu Asp Phe
225                 230                 235                 240

Lys Gln Leu Glu Ser Phe Tyr Ile Gln Thr Leu Leu Asp Ile Val Ser
            245                 250                 255

Ser Tyr Gly Lys Gly Tyr Val Val Trp Gln Glu Val Phe Asp Asn Lys
            260                 265                 270

Val Lys Ile Gln Pro Asp Thr Ile Ile Gln Val Trp Arg Glu Asp Ile
            275                 280                 285

Pro Val Asn Tyr Met Lys Glu Leu Glu Leu Val Thr Lys Ala Gly Phe
            290                 295                 300

Arg Ala Leu Leu Ser Ala Pro Trp Tyr Leu Asn Arg Ile Ser Tyr Gly
305                 310                 315                 320

Pro Asp Trp Lys Asp Phe Tyr Val Val Glu Pro Leu Ala Phe Glu Gly
            325                 330                 335

Thr Pro Glu Gln Lys Ala Leu Val Ile Gly Gly Glu Ala Cys Met Trp
            340                 345                 350

Gly Glu Tyr Val Asp Asn Thr Asn Leu Val Pro Arg Leu Trp Pro Arg
            355                 360                 365

Ala Gly Ala Val Ala Glu Arg Leu Trp Ser Asn Lys Leu Thr Ser Asp
370                 375                 380

Leu Thr Phe Ala Tyr Glu Arg Leu Ser His Phe Arg Cys Glu Leu Leu
385                 390                 395                 400

Arg Arg Gly Val Gln Ala Gln Pro Leu Asn Val Gly Phe Cys Glu Gln
            405                 410                 415

Glu Phe Glu Gln Thr
            420

<210> SEQ ID NO 15
<211> LENGTH: 191
<212> TYPE: PRT
<213> ORGANISM: HOMO SAPIENS

<400> SEQUENCE: 15

Met Thr Ser Ser Arg Leu Trp Phe Ser Leu Leu Ala Ala Phe
1               5                   10                  15

Ala Gly Arg Ala Thr Ala Leu Trp Pro Trp Pro Gln Asn Phe Gln Thr
            20                  25                  30

Ser Asp Gln Arg Tyr Val Leu Tyr Pro Asn Asn Phe Gln Phe Gln Tyr
            35                  40                  45

Asp Val Ser Ser Ala Ala Gln Pro Gly Cys Ser Val Leu Asp Glu Ala
        50                  55                  60

Phe Gln Arg Tyr Arg Asp Leu Leu Phe Gly Ser Gly Ser Trp Pro Arg
65                  70                  75                  80

Pro Tyr Leu Thr Gly Lys Arg His Thr Leu Glu Lys Asn Val Leu Val
            85                  90                  95

Val Ser Val Val Thr Pro Gly Cys Asn Gln Leu Pro Thr Leu Glu Ser
            100                 105                 110

Val Glu Asn Tyr Thr Leu Thr Ile Asn Asp Asp Gln Cys Leu Leu Leu
            115                 120                 125

Ser Glu Thr Val Trp Gly Ala Leu Arg Gly Leu Glu Thr Phe Ser Gln
```

```
                 130                 135                 140
Leu Val Trp Lys Ser Ala Glu Gly Thr Phe Phe Ile Asn Lys Thr Glu
145                 150                 155                 160

Ile Glu Asp Phe Pro Arg Phe Pro His Arg Gly Leu Leu Leu Asp Thr
                165                 170                 175

Ser Arg His Tyr Leu Pro Leu Ser Ser Ile Leu Asp Thr Leu Asp
                180                 185                 190

<210> SEQ ID NO 16
<211> LENGTH: 127
<212> TYPE: PRT
<213> ORGANISM: HOMO SAPIENS

<400> SEQUENCE: 16

Glu Leu Glu Leu Val Thr Lys Ala Gly Phe Arg Ala Leu Leu Ser Ala
1               5                   10                  15

Pro Trp Tyr Leu Asn Arg Ile Ser Tyr Gly Pro Asp Trp Lys Asp Phe
                20                  25                  30

Tyr Val Val Glu Pro Leu Ala Phe Glu Gly Thr Pro Glu Gln Lys Ala
            35                  40                  45

Leu Val Ile Gly Gly Glu Ala Cys Met Trp Gly Glu Tyr Val Asp Asn
        50                  55                  60

Thr Asn Leu Val Pro Arg Leu Trp Pro Arg Ala Gly Ala Val Ala Glu
65                  70                  75                  80

Arg Leu Trp Ser Asn Lys Leu Thr Ser Asp Leu Thr Phe Ala Tyr Glu
                85                  90                  95

Arg Leu Ser His Phe Arg Cys Glu Leu Leu Arg Arg Gly Val Gln Ala
                100                 105                 110

Gln Pro Leu Asn Val Gly Phe Cys Glu Gln Glu Phe Glu Gln Thr
            115                 120                 125

<210> SEQ ID NO 17
<211> LENGTH: 1590
<212> TYPE: DNA
<213> ORGANISM: HOMO SAPIENS

<400> SEQUENCE: 17
atgacaagct ccaggctttg gttttcgctg ctgctggcgg cagcgttcgc aggacgggcg      60
acggccctct ggccctggcc tcagaacttc caaacctccg accagcgcta cgtcctttac     120
ccgaacaact tcaattcca gtacgatgtc agctcggccg cgcagcccgg ctgctcagtc      180
ctcgacgagg ccttccagcg ctatcgtgac ctgcttttcg gttccgggtc ttggcccgt      240 ccttacctca cagggaaacg gcatacactg gagaagaatg tgttggttgt ctctgtagtc     300
acacctggat gtaaccagct tcctactttg gagtcagtgg agaattatac cctgaccata     360
aatgatgacc agtgtttact cctctctgag actgtctggg gagctctccg aggtctggag     420
acttttagcc agcttgtttg gaaatctgct gagggcacat tctttatcaa caagactgag     480
attgaggact tccccgctt tcctcaccgg ggcttgctgt tggatacatc tcgccattac     540
ctgccactct ctagcatcct ggacactctg gatgtcatgg cgtacaataa attgaacgtg     600
ttccactggc atctggtaga tgatccttcc ttcccatatg agagcttcac ttttccagag     660
ctcatgagaa aggggtccta caaccctgtc acccacatct acacagcaca ggatgtgaag     720
gaggtcattg aatacgcacg gctccggggt atccgtgtgc ttgcagagtt tgacactcct     780
ggccacactt tgtcctgggg accaggtatc cctggattac tgactccttg ctactctggg     840
```

```
tctgagccct ctggcacctt tggaccagtg aatcccagtc tcaataatac ctatgagttc    900
atgagcacat tcttcttaga agtcagctct gtcttcccag attttatct tcatcttgga    960 ggagatgagg ttgatttcac ctgctggaag tccaacccag agatccagga ctttatgagg   1020
aagaaaggct tcggtgagga cttcaagcag ctggagtcct tctacatcca gacgctgctg   1080
gacatcgtct cttcttatgg caagggctat gtggtgtggc aggaggtgtt tgataataaa   1140
gtaaagattc agccagacac aatcatacag gtgtggcgag aggatattcc agtgaactat   1200
atgaaggagc tggaactggt caccaaggcc ggcttccggg cccttctctc tgcccctgg    1260 tacctgaacc gtatatccta tggccctgac tggaaggatt tctacgtagt ggaacccctg   1320
gcatttgaag gtaccccgta gcagaaggct ctggtgattg tggagaggc ttgtatgtgg    1380 ggagaatatg tggacaacac aaacctggtc cccaggctct ggcccagagc aggggctgtt   1440
gccgaaaggc tgtggagcaa caagttgaca tctgacctga catttgccta tgaacgtttg   1500
tcacacttcc gctgtgagtt gctgaggcga ggtgtccagg cccaacccct caatgtaggc   1560
ttctgtgagc aggagtttga acagacctga                                    1590

<210> SEQ ID NO 18
<211> LENGTH: 1266
<212> TYPE: DNA
<213> ORGANISM: HOMO SAPIENS

<400> SEQUENCE: 18
tcctactttg gagtcagtgg agaattatac cctgaccata aatgatgacc agtgtttact     60
cctctctgag actgtctggg gagctctccg aggtctggag acttttagcc agcttgtttg    120
gaaatctgct gagggcacat tctttatcaa caagactgag attgaggact ttccccgctt    180
cctcaccggg gcttgctgtt ggatacatct cgccattacc tgccactctc tagcatcctg    240
gacactctgg atgtcatggc gtacaataaa ttgaacgtgt tccactggca tctggtagat    300
gatccttcct tcccatatga gagcttcact tttccagagc tcatgagaaa ggggtcctac    360
aaccctgtca cccacatcta cacagcacag gatgtgaagg aggtcattga atacgcacgg    420
ctccggggta tccgtgtgct tgcagagttt gacactcctg gccacacttt gtcctgggga    480
ccaggtatcc ctggattact gactccttgc tactctgggt ctgagccctc tggcaccttt    540
ggaccagtga atcccagtct caataatacc tatgagttca tgagcacatt cttcttagaa    600
gtcagctctg tcttcccaga ttttttatctt catcttggag gagatgaggt tgatttcacc    660
tgctggaagt ccaacccaga gatccaggac tttatgagga agaaaggctt cggtgaggac    720
ttcaagcagc tggagtcctt ctacatccag acgctgctgg acatcgtctc ttcttatggc    780
aagggctatg tggtgtggca ggaggtgttt gataataaag taaagattca gccagacaca    840
atcatacagg tgtggcgaga ggatattcca gtgaactata tgaaggagct ggaactggtc    900
accaaggccg gcttccgggc ccttctctct gcccccctggt acctgaaccg tatatcctat    960
ggccctgact ggaaggattt ctacgtagtg gaacccctgg catttgaagg tacccctgag   1020
cagaaggctc tggtgattgg tggagaggct tgtatgtggg gagaatatgt ggacaacaca   1080
aacctggtcc ccaggctctg gcccagagca ggggctgttg ccgaaaggct gtggagcaac   1140
aagttgacat ctgacctgac atttgcctat gaacgtttgt cacacttccg ctgtgagttg   1200
ctgaggcgag gtgtccaggc ccaacccctc aatgtaggct tctgtgagca ggagtttgaa   1260
cagacc                                                             1266
```

<210> SEQ ID NO 19
<211> LENGTH: 573
<212> TYPE: DNA
<213> ORGANISM: HOMO SAPIENS

<400> SEQUENCE: 19

```
atgacaagct ccaggctttg gttttcgctg ctgctggcgg cagcgttcgc aggacgggcg      60
acggccctct ggccctggcc tcagaacttc caaacctccg accagcgcta cgtcctttac     120
ccgaacaact ttcaattcca gtacgatgtc agctcggccg cgcagcccgg ctgctcagtc     180
ctcgacgagg ccttccagcg ctatcgtgac ctgcttttcg gttccgggtc ttggccccgt     240
ccttacctca cagggaaacg gcatacactg gagaagaatg tgttggttgt ctctgtagtc     300
acacctggat gtaaccagct tcctactttg gagtcagtgg agaattatac cctgaccata     360
aatgatgacc agtgtttact cctctctgag actgtctggg gagctctccg aggtctggag     420
acttttagcc agcttgtttg gaaatctgct gagggcacat tctttatcaa caagactgag     480
attgaggact tcccccgctt tcctcaccgg ggcttgctgt tggatacatc tcgccattac     540
ctgccactct ctagcatcct ggacactctg gat                                  573
```

<210> SEQ ID NO 20
<211> LENGTH: 378
<212> TYPE: DNA
<213> ORGANISM: HOMO SAPIENS

<400> SEQUENCE: 20

```
ctggaactgg tcaccaaggc cggcttccgg gcccttctct ctgcccctg gtacctgaac       60
cgtatatcct atggccctga ctggaaggat ttctacgtag tggaaccct ggcatttgaa      120
ggtaccctg agcagaaggc tctggtgatt ggtggagagg cttgtatgtg gggagaatat      180
gtggacaaca caaacctggt ccccaggctc tggcccagag caggggctgt tgccgaaagg     240
ctgtggagca acaagttgac atctgacctg acatttgcct atgaacgttt gtcacacttc     300
cgctgtgagt tgctgaggcg aggtgtccag gcccaacccc tcaatgtagg cttctgtgag     360
caggagtttg aacagacc                                                   378
```

<210> SEQ ID NO 21
<211> LENGTH: 556
<212> TYPE: PRT
<213> ORGANISM: HOMO SAPIENS

<400> SEQUENCE: 21

```
Met Glu Leu Cys Gly Leu Gly Leu Pro Arg Pro Pro Met Leu Leu Ala
1               5                   10                  15

Leu Leu Leu Ala Thr Leu Leu Ala Ala Met Leu Ala Leu Leu Thr Gln
            20                  25                  30

Val Ala Leu Val Val Gln Val Ala Glu Ala Ala Arg Ala Pro Ser Val
        35                  40                  45

Ser Ala Lys Pro Gly Pro Ala Leu Trp Pro Leu Pro Leu Ser Val Lys
    50                  55                  60

Met Thr Pro Asn Leu Leu His Leu Ala Pro Glu Asn Phe Tyr Ile Ser
65                  70                  75                  80

His Ser Pro Asn Ser Thr Ala Gly Pro Ser Cys Thr Leu Leu Glu Glu
                85                  90                  95

Ala Phe Arg Arg Tyr His Gly Tyr Ile Phe Gly Phe Tyr Lys Trp His
            100                 105                 110

His Glu Pro Ala Glu Phe Gln Ala Lys Thr Gln Val Gln Gln Leu Leu
```

```
            115                 120                 125
Val Ser Ile Thr Leu Gln Ser Glu Cys Asp Ala Phe Pro Asn Ile Ser
    130                 135                 140

Ser Asp Glu Ser Tyr Thr Leu Leu Val Lys Glu Pro Val Ala Val Leu
145                 150                 155                 160

Lys Ala Asn Arg Val Trp Gly Ala Leu Arg Gly Leu Glu Thr Phe Ser
                165                 170                 175

Gln Leu Val Tyr Gln Asp Ser Tyr Gly Thr Phe Thr Ile Asn Glu Ser
                180                 185                 190

Thr Ile Ile Asp Ser Pro Arg Phe Ser His Arg Gly Ile Leu Ile Asp
            195                 200                 205

Thr Ser Arg His Tyr Leu Pro Val Lys Ile Ile Leu Lys Thr Leu Asp
        210                 215                 220

Ala Met Ala Phe Asn Lys Phe Asn Val Leu His Trp His Ile Val Asp
225                 230                 235                 240

Asp Gln Ser Phe Pro Tyr Gln Ser Ile Thr Phe Pro Glu Leu Ser Asn
                245                 250                 255

Lys Gly Ser Tyr Ser Leu Ser His Val Tyr Thr Pro Asn Asp Val Arg
            260                 265                 270

Met Val Ile Glu Tyr Ala Arg Leu Arg Gly Ile Arg Val Leu Pro Glu
        275                 280                 285

Phe Asp Thr Pro Gly His Thr Leu Ser Trp Gly Lys Gly Gln Lys Asp
290                 295                 300

Leu Leu Thr Pro Cys Tyr Ser Arg Gln Asn Lys Leu Asp Ser Phe Gly
305                 310                 315                 320

Pro Ile Asn Pro Thr Leu Asn Thr Thr Tyr Ser Phe Leu Thr Thr Phe
                325                 330                 335

Phe Lys Glu Ile Ser Glu Val Phe Pro Asp Gln Phe Ile His Leu Gly
            340                 345                 350

Gly Asp Glu Val Glu Phe Lys Cys Trp Glu Ser Asn Pro Lys Ile Gln
        355                 360                 365

Asp Phe Met Arg Gln Lys Gly Phe Gly Thr Asp Phe Lys Lys Leu Glu
    370                 375                 380

Ser Phe Tyr Ile Gln Lys Val Leu Asp Ile Ile Ala Thr Ile Asn Lys
385                 390                 395                 400

Gly Ser Ile Val Trp Gln Glu Val Phe Asp Lys Ala Lys Leu Ala
                405                 410                 415

Pro Gly Thr Ile Val Glu Val Trp Lys Asp Ser Ala Tyr Pro Glu Glu
                420                 425                 430

Leu Ser Arg Val Thr Ala Ser Gly Phe Pro Val Ile Leu Ser Ala Pro
        435                 440                 445

Trp Tyr Leu Asp Leu Ile Ser Tyr Gly Gln Asp Trp Arg Lys Tyr Tyr
    450                 455                 460

Lys Val Glu Pro Leu Asp Phe Gly Gly Thr Gln Lys Gln Lys Gln Leu
465                 470                 475                 480

Phe Ile Gly Gly Glu Ala Cys Leu Trp Gly Glu Tyr Val Asp Ala Thr
                485                 490                 495

Asn Leu Thr Pro Arg Leu Trp Pro Arg Ala Ser Ala Val Gly Glu Arg
                500                 505                 510

Leu Trp Ser Ser Lys Asp Val Arg Asp Met Asp Asp Ala Tyr Asp Arg
        515                 520                 525

Leu Thr Arg His Arg Cys Arg Met Val Glu Arg Gly Ile Ala Ala Gln
    530                 535                 540
```

```
Pro Leu Tyr Ala Gly Tyr Cys Asn His Glu Asn Met
545                 550                 555

<210> SEQ ID NO 22
<211> LENGTH: 1857
<212> TYPE: DNA
<213> ORGANISM: HOMO SAPIENS

<400> SEQUENCE: 22
ctgatccggg ccgggcggga agtcgggtcc cgaggctccg gctcggcaga ccgggcggaa      60
agcagccgag cggccatgga gctgtgcggg ctggggctgc ccggccgcc catgctgctg     120
gcgctgctgt tggcgacact gctggcggcg atgttggcgc tgctgactca ggtggcgctg     180
gtggtgcagg tggcggaggc ggctcgggcc ccgagcgtct cggccaagcc ggggccggcg     240
ctgtggcccc tgccgctctc ggtgaagatg accccgaacc tgctgcatct cgccccggag     300
aacttctaca tcagccacag ccccaattcc acggcgggcc cctcctgcac cctgctggag     360
gaagcgtttc gacgatatca tggctatatt tttggtttct acaagtggca tcatgaacct     420
gctgaattcc aggctaaaac ccaggttcag caacttcttg tctcaatcac ccttcagtca     480
gagtgtgatg ctttccccaa catatcttca gatgagtctt atactttact gtgaaagaa     540
ccagtggctg tccttaaggc caacagagtt tggggagcat tacgaggttt agagaccttt     600
agccagttag tttatcaaga ttcttatgga actttcacca tcaatgaatc caccattatt     660
gattctccaa ggttttctca cagaggaatt ttgattgata catccagaca ttatctgcca     720
gttaagatta ttcttaaaac tctggatgcc atggctttta ataagtttaa tgttcttcac     780
tggcacatag ttgatgacca gtcttttccca tatcagagca tcacttttcc tgagttaagc     840
aataaaggaa gctattcttt gtctcatgtt tatacaccaa atgatgtccg tatggtgatt     900
gaatatgcca gattacgagg aattcgagtc ctgccagaat ttgataccc tgggcataca     960
ctatcttggg gaaaaggtca gaaagacctc ctgactccat gttacagtag acaaaacaag    1020
ttggactctt ttggacctat aaaccctact ctgaatacaa catacagctt ccttactaca    1080
ttttcaaag aaattagtga ggtgtttcca gatcaattca ttcatttggg aggagatgaa    1140
gtggaattta atgttgggga atcaaatcca aaaattcaag atttcatgag gcaaaaggc    1200
tttggcacag attttaagaa actagaatct ttctacattc aaaaggttt ggatattatt    1260
gcaaccataa acaagggatc cattgtctgg caggaggttt ttgatgataa agcaaagctt    1320
gcgccgggca caatagttga agtatggaaa gacagcgcat atcctgagga actcagtaga    1380
gtcacagcat ctggcttccc tgtaatcctt tctgctcctt ggtacttaga tttgattagc    1440
tatgacaag attggaggaa atactataaa gtggaacctc ttgattttgg cggtactcag    1500
aaacagaaac aacttttcat tggtggagaa gcttgtctat ggggagaata tgtggatgca    1560
actaacctca ctccaagatt atggcctcgg gcaagtgctg ttggtgagag actctggagt    1620
tccaaagatg tcagagatat ggatgacgcc tatgacagac tgacaaggca ccgctgcagg    1680
atggtcgaac gtggaatagc tgcacaacct ctttatgctg atattgtaa ccatgagaac    1740
atgtaaaaaa tggagggaaa aaaggccaca gcaatctgta ctacaatcaa ctttattttg    1800
aaatcatgta aaataagata ttagactttt ttgaataaaa tatttttatt gattgaa       1857

<210> SEQ ID NO 23
<211> LENGTH: 736
<212> TYPE: PRT
<213> ORGANISM: ARTIFICIAL
```

<220> FEATURE:
<223> OTHER INFORMATION: Chimeric protein

<400> SEQUENCE: 23

```
Met Ala Gly Pro Ala Thr Gln Ser Pro Met Lys Leu Met Ala Leu Gln
1               5                   10                  15

Leu Leu Leu Trp His Ser Ala Leu Trp Thr Val Gln Glu Ala Thr Pro
            20                  25                  30

Leu Gly Pro Ala Ser Ser Leu Pro Gln Ser Phe Leu Leu Lys Cys Leu
        35                  40                  45

Glu Gln Val Arg Lys Ile Gln Gly Asp Gly Ala Ala Leu Gln Glu Lys
    50                  55                  60

Leu Val Ser Glu Cys Ala Thr Tyr Lys Leu Cys His Pro Glu Glu Leu
65                  70                  75                  80

Val Leu Leu Gly His Ser Leu Gly Ile Pro Trp Ala Pro Leu Ser Ser
                85                  90                  95

Cys Pro Ser Gln Ala Leu Gln Leu Ala Gly Cys Leu Ser Gln Leu His
                100                 105                 110

Ser Gly Leu Phe Leu Tyr Gln Gly Leu Leu Gln Ala Leu Glu Gly Ile
            115                 120                 125

Ser Pro Glu Leu Gly Pro Thr Leu Asp Thr Leu Gln Leu Asp Val Ala
        130                 135                 140

Asp Phe Ala Thr Thr Ile Trp Gln Gln Met Glu Glu Leu Gly Met Ala
145                 150                 155                 160

Pro Ala Leu Gln Pro Thr Gln Gly Ala Met Pro Ala Phe Ala Ser Ala
                165                 170                 175

Phe Gln Arg Arg Ala Gly Gly Val Leu Val Ala Ser His Leu Gln Ser
                180                 185                 190

Phe Leu Glu Val Ser Tyr Arg Val Leu Arg His Leu Ala Gln Pro Met
            195                 200                 205

Thr Ser Ser Arg Leu Trp Phe Ser Leu Leu Ala Ala Ala Phe Ala
        210                 215                 220

Gly Arg Ala Thr Ala Leu Trp Pro Trp Pro Gln Asn Phe Gln Thr Ser
225                 230                 235                 240

Asp Gln Arg Tyr Val Leu Tyr Pro Asn Asn Phe Gln Phe Gln Tyr Asp
                245                 250                 255

Val Ser Ser Ala Ala Gln Pro Gly Cys Ser Val Leu Asp Glu Ala Phe
            260                 265                 270

Gln Arg Tyr Arg Asp Leu Leu Phe Gly Ser Gly Ser Trp Pro Arg Pro
        275                 280                 285

Tyr Leu Thr Gly Lys Arg His Thr Leu Glu Lys Asn Val Leu Val Val
    290                 295                 300

Ser Val Val Thr Pro Gly Cys Asn Gln Leu Pro Thr Leu Glu Ser Val
305                 310                 315                 320

Glu Asn Tyr Thr Leu Thr Ile Asn Asp Asp Gln Cys Leu Leu Leu Ser
                325                 330                 335

Glu Thr Val Trp Gly Ala Leu Arg Gly Leu Glu Thr Phe Ser Gln Leu
            340                 345                 350

Val Trp Lys Ser Ala Glu Gly Thr Phe Phe Ile Asn Lys Thr Glu Ile
        355                 360                 365

Glu Asp Phe Pro Arg Phe Pro His Arg Gly Leu Leu Leu Asp Thr Ser
    370                 375                 380

Arg His Tyr Leu Pro Leu Ser Ser Ile Leu Asp Thr Leu Asp Val Met
385                 390                 395                 400
```

Ala Tyr Asn Lys Leu Asn Val Phe His Trp His Leu Val Asp Asp Pro
            405                 410                 415

Ser Phe Pro Tyr Glu Ser Phe Thr Phe Pro Glu Leu Met Arg Lys Gly
        420                 425                 430

Ser Tyr Asn Pro Val Thr His Ile Tyr Thr Ala Gln Asp Val Lys Glu
        435                 440                 445

Val Ile Glu Tyr Ala Arg Leu Arg Gly Ile Arg Val Leu Ala Glu Phe
    450                 455                 460

Asp Thr Pro Gly His Thr Leu Ser Trp Gly Pro Gly Ile Pro Gly Leu
465                 470                 475                 480

Leu Thr Pro Cys Tyr Ser Gly Ser Glu Pro Ser Gly Thr Phe Gly Pro
                485                 490                 495

Val Asn Pro Ser Leu Asn Asn Thr Tyr Glu Phe Met Ser Thr Phe Phe
            500                 505                 510

Leu Glu Val Ser Ser Val Phe Pro Asp Phe Tyr Leu His Leu Gly Gly
        515                 520                 525

Asp Glu Val Asp Phe Thr Cys Trp Lys Ser Asn Pro Glu Ile Gln Asp
        530                 535                 540

Phe Met Arg Lys Lys Gly Phe Gly Glu Asp Phe Lys Gln Leu Glu Ser
545                 550                 555                 560

Phe Tyr Ile Gln Thr Leu Leu Asp Ile Val Ser Ser Tyr Gly Lys Gly
                565                 570                 575

Tyr Val Val Trp Gln Glu Val Phe Asp Asn Lys Val Lys Ile Gln Pro
            580                 585                 590

Asp Thr Ile Ile Gln Val Trp Arg Glu Asp Ile Pro Val Asn Tyr Met
                595                 600                 605

Lys Glu Leu Glu Leu Val Thr Lys Ala Gly Phe Arg Ala Leu Leu Ser
        610                 615                 620

Ala Pro Trp Tyr Leu Asn Arg Ile Ser Tyr Gly Pro Asp Trp Lys Asp
625                 630                 635                 640

Phe Tyr Val Val Glu Pro Leu Ala Phe Glu Gly Thr Pro Glu Gln Lys
                645                 650                 655

Ala Leu Val Ile Gly Gly Glu Ala Cys Met Trp Gly Glu Tyr Val Asp
            660                 665                 670

Asn Thr Asn Leu Val Pro Arg Leu Trp Pro Arg Ala Gly Ala Val Ala
        675                 680                 685

Glu Arg Leu Trp Ser Asn Lys Leu Thr Ser Asp Leu Thr Phe Ala Tyr
690                 695                 700

Glu Arg Leu Ser His Phe Arg Cys Glu Leu Leu Arg Arg Gly Val Gln
705                 710                 715                 720

Ala Gln Pro Leu Asn Val Gly Phe Cys Glu Gln Glu Phe Glu Gln Thr
                725                 730                 735

<210> SEQ ID NO 24
<211> LENGTH: 628
<212> TYPE: PRT
<213> ORGANISM: ARTIFICIAL
<220> FEATURE:
<223> OTHER INFORMATION: Chimeric protein

<400> SEQUENCE: 24

Met Ala Gly Pro Ala Thr Gln Ser Pro Met Lys Leu Met Ala Leu Gln
1               5                   10                  15

Leu Leu Leu Trp His Ser Ala Leu Trp Thr Val Gln Glu Ala Thr Pro
            20                  25                  30

Leu Gly Pro Ala Ser Ser Leu Pro Gln Ser Phe Leu Leu Lys Cys Leu
        35                  40                  45

Glu Gln Val Arg Lys Ile Gln Gly Asp Gly Ala Ala Leu Gln Glu Lys
 50                  55                  60

Leu Val Ser Glu Cys Ala Thr Tyr Lys Leu Cys His Pro Glu Glu Leu
 65                  70                  75                  80

Val Leu Leu Gly His Ser Leu Gly Ile Pro Trp Ala Pro Leu Ser Ser
                 85                  90                  95

Cys Pro Ser Gln Ala Leu Gln Leu Ala Gly Cys Leu Ser Gln Leu His
             100                 105                 110

Ser Gly Leu Phe Leu Tyr Gln Gly Leu Leu Gln Ala Leu Glu Gly Ile
         115                 120                 125

Ser Pro Glu Leu Gly Pro Thr Leu Asp Thr Leu Gln Leu Asp Val Ala
     130                 135                 140

Asp Phe Ala Thr Thr Ile Trp Gln Gln Met Glu Glu Leu Gly Met Ala
145                 150                 155                 160

Pro Ala Leu Gln Pro Thr Gln Gly Ala Met Pro Ala Phe Ala Ser Ala
                165                 170                 175

Phe Gln Arg Arg Ala Gly Gly Val Leu Val Ala Ser His Leu Gln Ser
            180                 185                 190

Phe Leu Glu Val Ser Tyr Arg Val Leu Arg His Leu Ala Gln Pro Thr
        195                 200                 205

Leu Glu Ser Val Glu Asn Tyr Thr Leu Thr Ile Asn Asp Asp Gln Cys
    210                 215                 220

Leu Leu Leu Ser Glu Thr Val Trp Gly Ala Leu Arg Gly Leu Glu Thr
225                 230                 235                 240

Phe Ser Gln Leu Val Trp Lys Ser Ala Glu Gly Thr Phe Phe Ile Asn
                245                 250                 255

Lys Thr Glu Ile Glu Asp Phe Pro Arg Phe Pro His Arg Gly Leu Leu
            260                 265                 270

Leu Asp Thr Ser Arg His Tyr Leu Pro Leu Ser Ser Ile Leu Asp Thr
        275                 280                 285

Leu Asp Val Met Ala Tyr Asn Lys Leu Asn Val Phe His Trp His Leu
    290                 295                 300

Val Asp Asp Pro Ser Phe Pro Tyr Glu Ser Phe Thr Phe Pro Glu Leu
305                 310                 315                 320

Met Arg Lys Gly Ser Tyr Asn Pro Val Thr His Ile Tyr Thr Ala Gln
                325                 330                 335

Asp Val Lys Glu Val Ile Glu Tyr Ala Arg Leu Arg Gly Ile Arg Val
            340                 345                 350

Leu Ala Glu Phe Asp Thr Pro Gly His Thr Leu Ser Trp Gly Pro Gly
        355                 360                 365

Ile Pro Gly Leu Leu Thr Pro Cys Tyr Ser Gly Ser Glu Pro Ser Gly
    370                 375                 380

Thr Phe Gly Pro Val Asn Pro Ser Leu Asn Asn Thr Tyr Glu Phe Met
385                 390                 395                 400

Ser Thr Phe Phe Leu Glu Val Ser Ser Val Phe Pro Asp Phe Tyr Leu
                405                 410                 415

His Leu Gly Gly Asp Glu Val Asp Phe Thr Cys Trp Lys Ser Asn Pro
            420                 425                 430

Glu Ile Gln Asp Phe Met Arg Lys Lys Gly Phe Gly Glu Asp Phe Lys
        435                 440                 445

Gln Leu Glu Ser Phe Tyr Ile Gln Thr Leu Leu Asp Ile Val Ser Ser
450                 455                 460

Tyr Gly Lys Gly Tyr Val Val Trp Gln Glu Val Phe Asp Asn Lys Val
465                 470                 475                 480

Lys Ile Gln Pro Asp Thr Ile Ile Gln Val Trp Arg Glu Asp Ile Pro
                485                 490                 495

Val Asn Tyr Met Lys Glu Leu Glu Leu Val Thr Lys Ala Gly Phe Arg
                500                 505                 510

Ala Leu Leu Ser Ala Pro Trp Tyr Leu Asn Arg Ile Ser Tyr Gly Pro
                515                 520                 525

Asp Trp Lys Asp Phe Tyr Val Val Glu Pro Leu Ala Phe Glu Gly Thr
530                 535                 540

Pro Glu Gln Lys Ala Leu Val Ile Gly Gly Glu Ala Cys Met Trp Gly
545                 550                 555                 560

Glu Tyr Val Asp Asn Thr Asn Leu Val Pro Arg Leu Trp Pro Arg Ala
                565                 570                 575

Gly Ala Val Ala Glu Arg Leu Trp Ser Asn Lys Leu Thr Ser Asp Leu
                580                 585                 590

Thr Phe Ala Tyr Glu Arg Leu Ser His Phe Arg Cys Glu Leu Leu Arg
                595                 600                 605

Arg Gly Val Gln Ala Gln Pro Leu Asn Val Gly Phe Cys Glu Gln Glu
                610                 615                 620

Phe Glu Gln Thr
625

<210> SEQ ID NO 25
<211> LENGTH: 398
<212> TYPE: PRT
<213> ORGANISM: ARTIFICIAL
<220> FEATURE:
<223> OTHER INFORMATION: Chimeric protein

<400> SEQUENCE: 25

Met Ala Gly Pro Ala Thr Gln Ser Pro Met Lys Leu Met Ala Leu Gln
1               5                   10                  15

Leu Leu Leu Trp His Ser Ala Leu Trp Thr Val Gln Glu Ala Thr Pro
                20                  25                  30

Leu Gly Pro Ala Ser Ser Leu Pro Gln Ser Phe Leu Leu Lys Cys Leu
                35                  40                  45

Glu Gln Val Arg Lys Ile Gln Gly Asp Gly Ala Ala Leu Gln Glu Lys
50                  55                  60

Leu Val Ser Glu Cys Ala Thr Tyr Lys Leu Cys His Pro Glu Glu Leu
65                  70                  75                  80

Val Leu Leu Gly His Ser Leu Gly Ile Pro Trp Ala Pro Leu Ser Ser
                85                  90                  95

Cys Pro Ser Gln Ala Leu Gln Leu Ala Gly Cys Leu Ser Gln Leu His
                100                 105                 110

Ser Gly Leu Phe Leu Tyr Gln Gly Leu Leu Gln Ala Leu Glu Gly Ile
                115                 120                 125

Ser Pro Glu Leu Gly Pro Thr Leu Asp Thr Leu Gln Leu Asp Val Ala
130                 135                 140

Asp Phe Ala Thr Thr Ile Trp Gln Gln Met Glu Glu Leu Gly Met Ala
145                 150                 155                 160

Pro Ala Leu Gln Pro Thr Gln Gly Ala Met Pro Ala Phe Ala Ser Ala
                165                 170                 175

```
Phe Gln Arg Arg Ala Gly Gly Val Leu Val Ala Ser His Leu Gln Ser
            180                 185                 190

Phe Leu Glu Val Ser Tyr Arg Val Leu Arg His Leu Ala Gln Pro Met
            195                 200                 205

Thr Ser Ser Arg Leu Trp Phe Ser Leu Leu Ala Ala Ala Phe Ala
        210                 215                 220

Gly Arg Ala Thr Ala Leu Trp Pro Trp Pro Gln Asn Phe Gln Thr Ser
225                 230                 235                 240

Asp Gln Arg Tyr Val Leu Tyr Pro Asn Asn Phe Gln Phe Gln Tyr Asp
            245                 250                 255

Val Ser Ser Ala Ala Gln Pro Gly Cys Ser Val Leu Asp Glu Ala Phe
            260                 265                 270

Gln Arg Tyr Arg Asp Leu Leu Phe Gly Ser Gly Ser Trp Pro Arg Pro
            275                 280                 285

Tyr Leu Thr Gly Lys Arg His Thr Leu Glu Lys Asn Val Leu Val Val
            290                 295                 300

Ser Val Val Thr Pro Gly Cys Asn Gln Leu Pro Thr Leu Glu Ser Val
305                 310                 315                 320

Glu Asn Tyr Thr Leu Thr Ile Asn Asp Asp Gln Cys Leu Leu Leu Ser
            325                 330                 335

Glu Thr Val Trp Gly Ala Leu Arg Gly Leu Glu Thr Phe Ser Gln Leu
            340                 345                 350

Val Trp Lys Ser Ala Glu Gly Thr Phe Phe Ile Asn Lys Thr Glu Ile
            355                 360                 365

Glu Asp Phe Pro Arg Phe Pro His Arg Gly Leu Leu Leu Asp Thr Ser
            370                 375                 380

Arg His Tyr Leu Pro Leu Ser Ser Ile Leu Asp Thr Leu Asp
385                 390                 395

<210> SEQ ID NO 26
<211> LENGTH: 696
<212> TYPE: PRT
<213> ORGANISM: ARTIFICIAL
<220> FEATURE:
<223> OTHER INFORMATION: Chimeric protein

<400> SEQUENCE: 26

Met His Trp Gly Thr Leu Cys Gly Phe Leu Trp Leu Trp Pro Tyr Leu
1               5                   10                  15

Phe Tyr Val Gln Ala Val Pro Ile Gln Lys Val Gln Asp Asp Thr Lys
            20                  25                  30

Thr Leu Ile Lys Thr Ile Val Thr Arg Ile Asn Asp Ile Ser His Thr
        35                  40                  45

Gln Ser Val Ser Ser Lys Gln Lys Val Thr Gly Leu Asp Phe Ile Pro
    50                  55                  60

Gly Leu His Pro Ile Leu Thr Leu Ser Lys Met Asp Gln Thr Leu Ala
65                  70                  75                  80

Val Tyr Gln Gln Ile Leu Thr Ser Met Pro Ser Arg Asn Val Ile Gln
            85                  90                  95

Ile Ser Asn Asp Leu Glu Asn Leu Arg Asp Leu Leu His Val Leu Ala
            100                 105                 110

Phe Ser Lys Ser Cys His Leu Pro Trp Ala Ser Gly Leu Glu Thr Leu
        115                 120                 125

Asp Ser Leu Gly Gly Val Leu Glu Ala Ser Gly Tyr Ser Thr Glu Val
    130                 135                 140
```

```
Val Ala Leu Ser Arg Leu Gln Gly Ser Leu Gln Asp Met Leu Trp Gln
145                 150                 155                 160
Leu Asp Leu Ser Pro Gly Cys Met Thr Ser Ser Arg Leu Trp Phe Ser
                165                 170                 175
Leu Leu Leu Ala Ala Ala Phe Ala Gly Arg Ala Thr Ala Leu Trp Pro
            180                 185                 190
Trp Pro Gln Asn Phe Gln Thr Ser Asp Gln Arg Tyr Val Leu Tyr Pro
        195                 200                 205
Asn Asn Phe Gln Phe Gln Tyr Asp Val Ser Ser Ala Ala Gln Pro Gly
    210                 215                 220
Cys Ser Val Leu Asp Glu Ala Phe Gln Arg Tyr Arg Asp Leu Leu Phe
225                 230                 235                 240
Gly Ser Gly Ser Trp Pro Arg Pro Tyr Leu Thr Gly Lys Arg His Thr
                245                 250                 255
Leu Glu Lys Asn Val Leu Val Val Ser Val Val Thr Pro Gly Cys Asn
            260                 265                 270
Gln Leu Pro Thr Leu Glu Ser Val Glu Asn Tyr Thr Leu Thr Ile Asn
        275                 280                 285
Asp Asp Gln Cys Leu Leu Leu Ser Glu Thr Val Trp Gly Ala Leu Arg
    290                 295                 300
Gly Leu Glu Thr Phe Ser Gln Leu Val Trp Lys Ser Ala Glu Gly Thr
305                 310                 315                 320
Phe Phe Ile Asn Lys Thr Glu Ile Glu Asp Phe Pro Arg Phe Pro His
                325                 330                 335
Arg Gly Leu Leu Leu Asp Thr Ser Arg His Tyr Leu Pro Leu Ser Ser
            340                 345                 350
Ile Leu Asp Thr Leu Asp Val Met Ala Tyr Asn Lys Leu Asn Val Phe
        355                 360                 365
His Trp His Leu Val Asp Asp Pro Ser Phe Pro Tyr Glu Ser Phe Thr
    370                 375                 380
Phe Pro Glu Leu Met Arg Lys Gly Ser Tyr Asn Pro Val Thr His Ile
385                 390                 395                 400
Tyr Thr Ala Gln Asp Val Lys Glu Val Ile Glu Tyr Ala Arg Leu Arg
                405                 410                 415
Gly Ile Arg Val Leu Ala Glu Phe Asp Thr Pro Gly His Thr Leu Ser
            420                 425                 430
Trp Gly Pro Gly Ile Pro Gly Leu Leu Thr Pro Cys Tyr Ser Gly Ser
        435                 440                 445
Glu Pro Ser Gly Thr Phe Gly Pro Val Asn Pro Ser Leu Asn Asn Thr
    450                 455                 460
Tyr Glu Phe Met Ser Thr Phe Phe Leu Glu Val Ser Ser Val Phe Pro
465                 470                 475                 480
Asp Phe Tyr Leu His Leu Gly Gly Asp Glu Val Asp Phe Thr Cys Trp
                485                 490                 495
Lys Ser Asn Pro Glu Ile Gln Asp Phe Met Arg Lys Gly Phe Gly
            500                 505                 510
Glu Asp Phe Lys Gln Leu Glu Ser Phe Tyr Ile Gln Thr Leu Leu Asp
        515                 520                 525
Ile Val Ser Ser Tyr Gly Lys Gly Tyr Val Val Trp Gln Glu Val Phe
    530                 535                 540
Asp Asn Lys Val Lys Ile Gln Pro Asp Thr Ile Ile Gln Val Trp Arg
545                 550                 555                 560
Glu Asp Ile Pro Val Asn Tyr Met Lys Glu Leu Glu Leu Val Thr Lys
```

```
                        565                 570                 575
Ala Gly Phe Arg Ala Leu Leu Ser Ala Pro Trp Tyr Leu Asn Arg Ile
                580                 585                 590

Ser Tyr Gly Pro Asp Trp Lys Asp Phe Tyr Val Val Glu Pro Leu Ala
            595                 600                 605

Phe Glu Gly Thr Pro Glu Gln Lys Ala Leu Val Ile Gly Gly Glu Ala
        610                 615                 620

Cys Met Trp Gly Glu Tyr Val Asp Asn Thr Asn Leu Val Pro Arg Leu
625                 630                 635                 640

Trp Pro Arg Ala Gly Ala Val Ala Glu Arg Leu Trp Ser Asn Lys Leu
                645                 650                 655

Thr Ser Asp Leu Thr Phe Ala Tyr Glu Arg Leu Ser His Phe Arg Cys
            660                 665                 670

Glu Leu Leu Arg Arg Gly Val Gln Ala Gln Pro Leu Asn Val Gly Phe
        675                 680                 685

Cys Glu Gln Glu Phe Glu Gln Thr
    690                 695

<210> SEQ ID NO 27
<211> LENGTH: 219
<212> TYPE: PRT
<213> ORGANISM: ESCHERICHIA COLI

<400> SEQUENCE: 27

Met Lys Phe Asn Leu Ile Asp Ile Glu Asp Trp Asn Arg Lys Pro Tyr
1               5                   10                  15

Phe Glu His Tyr Leu Asn Ala Val Arg Cys Thr Tyr Ser Met Thr Ala
            20                  25                  30

Asn Ile Glu Ile Thr Gly Leu Leu Arg Glu Ile Lys Leu Lys Gly Leu
        35                  40                  45

Lys Leu Tyr Pro Thr Leu Ile Tyr Ile Thr Thr Val Val Asn Arg
    50                  55                  60

His Lys Glu Phe Arg Thr Cys Phe Asp Gln Lys Gly Lys Leu Gly Tyr
65                  70                  75                  80

Trp Asp Ser Met Asn Pro Ser Tyr Thr Val Phe His Lys Asp Asn Glu
                85                  90                  95

Thr Phe Ser Ser Ile Trp Thr Glu Tyr Asp Glu Asn Phe Pro Arg Phe
            100                 105                 110

Tyr Tyr Asn Tyr Leu Glu Asp Ile Arg Asn Tyr Ser Asp Val Leu Asn
        115                 120                 125

Phe Met Pro Lys Thr Gly Glu Pro Ala Asn Thr Ile Asn Val Ser Ser
    130                 135                 140

Ile Pro Trp Val Asn Phe Thr Gly Phe Asn Leu Asn Ile Tyr Asn Asp
145                 150                 155                 160

Ala Thr Tyr Leu Ile Pro Ile Phe Thr Leu Gly Lys Tyr Phe Gln Gln
                165                 170                 175

Asp Asn Lys Ile Leu Leu Pro Met Ser Val Gln Val His Ala Val
            180                 185                 190

Cys Asp Gly Tyr His Ile Ser Arg Phe Phe Asn Glu Ala Gln Glu Leu
        195                 200                 205

Ala Ser Asn Tyr Glu Thr Trp Leu Gly Glu Lys
    210                 215

<210> SEQ ID NO 28
<211> LENGTH: 660
```

<212> TYPE: DNA
<213> ORGANISM: ESCHERICHIA COLI

<400> SEQUENCE: 28

```
atgaaattta atttgataga tattgaggat tggaatagaa agccatactt tgagcattat    60
ttaaatgcgg ttaggtgcac ttacagtatg actgcaaata tagagataac tggtttactg   120
cgtgaaatta aacttaaggg cctgaaactg taccctacgc ttatttatat catcacaact   180
gtggttaacc gtcacaagga gttccgcacc tgttttgatc aaaaaggtaa gttaggatac   240
tgggatagta tgaacccaag ttatactgtc tttcataagg ataacgaaac ttttcaagt    300
atttggacag agtatgacga gaacttccca cgttttttact ataattaccct tgaggatatt   360
agaaactata gcgacgtttt gaatttcatg cctaagacag gtgaacctgc taatacaatt   420
aatgtgtcca gcattccttg ggtgaatttt accggattca acctgaatat atacaatgat   480
gcaacatatc taatccctat ttttactttg ggtaagtatt ttcagcagga ataaaaatt    540
ttattaccta tgtctgtaca ggtgcatcat gcggtttgcg acggttatca tataagcaga   600
ttttttaatg aggcacagga attagcgtca aattatgaga catggttagg agaaaaataa   660
```

<210> SEQ ID NO 29
<211> LENGTH: 362
<212> TYPE: PRT
<213> ORGANISM: ESCHERICHIA COLI

<400> SEQUENCE: 29

```
Met Leu Arg Trp Ile Val Gln Leu Phe Phe Ile Leu Val Gly Gly Thr
1               5                   10                  15

Leu Gly Phe Ile Phe Ile Pro Asp Leu Met Ala Trp Met Ser Ile Gln
            20                  25                  30

Asp Pro Thr Trp Leu Thr Asn Pro Tyr Val Gly Thr Val Met Gly Ala
        35                  40                  45

Ile Ile Leu Phe Leu Leu Thr Phe Trp Leu Cys Asp Tyr Ile Val His
    50                  55                  60

Leu Met Arg Val Thr Glu Glu Met Ile Val Lys Ala Pro Val Thr Asp
65                  70                  75                  80

Val Leu Phe Gly Thr Met Gly Leu Ile Ile Gly Leu Ile Val Ala Phe
                85                  90                  95

Leu Val Gly Ile Pro Leu Gly Asn Phe Ser Ile Pro Val Ser Thr
            100                 105                 110

Val Leu Pro Ile Phe Ile Thr Phe Phe Leu Gly Tyr Phe Gly Phe Gln
        115                 120                 125

Ile Gly Phe Lys Lys Arg Asp Glu Leu Ile His Leu Met Ser Ile Thr
    130                 135                 140

Arg Gly Phe Gly Lys Lys Lys Asp Glu Glu Ser Glu Ala Arg Gly
145                 150                 155                 160

Ser Lys Leu Lys Ile Leu Asp Thr Ser Val Ile Ile Asp Gly Arg Ile
                165                 170                 175

Ala Asp Ile Cys Lys Thr Gly Phe Leu Glu Gly Thr Leu Val Ile Pro
            180                 185                 190

Gly Phe Val Leu Glu Glu Leu Gln His Ile Ala Asp Ser Ser Asp Val
        195                 200                 205

Leu Lys Arg Asn Arg Gly Arg Arg Gly Leu Asp Ile Leu Asn Lys Ile
    210                 215                 220

Gln Lys Glu Leu Pro Ile Asn Val Glu Ile Tyr Glu Gly Asp Phe Glu
225                 230                 235                 240
```

```
Asp Ile Gln Glu Val Asp Ser Lys Leu Val Lys Leu Ala Lys Val Thr
                245                 250                 255

Glu Gly Met Val Val Thr Asn Asp Phe Asn Leu Asn Lys Val Cys Glu
        260                 265                 270

Leu Gln Gly Val Gln Val Leu Asn Ile Asn Asp Leu Ala Asn Ala Val
    275                 280                 285

Lys Pro Val Val Leu Pro Gly Glu Leu Asn Val Gln Val Ile Lys
290                 295                 300

Asp Gly Lys Glu Gln Asn Gln Gly Val Ala Tyr Leu Asp Asp Gly Thr
305                 310                 315                 320

Met Ile Val Val Glu Gly Gly Arg Asp Tyr Ile Gly Lys His Val Glu
                325                 330                 335

Val Val Thr Ser Val Leu Gln Thr Ser Ala Gly Arg Met Ile Phe
            340                 345                 350

Ala Lys Pro Lys Leu Leu Glu Lys Ala Leu
        355                 360

<210> SEQ ID NO 30
<211> LENGTH: 1089
<212> TYPE: DNA
<213> ORGANISM: ESCHERICHIA COLI

<400> SEQUENCE: 30
atgttaagat ggatagtcca attgtttttt attttagttg gtggtacact cggtttatt         60 tttattcctg accttatggc atggatgagc attcaagatc ccacatggct taccaatccg       120
tatgtaggga cggtcatggg tgcaatcatt ttattttgc taaccttttg gctatgtgat        180
tatattgttc atttaatgcg agttacggaa gaaatgattg tgaaagcgcc tgtcaccgat       240 gtgcttttg gaacgatggg attgattatt ggccttattg ttgccttctt agtagggatt        300
cctttaggta atttctccat tcctgtcgtg agcacggttt tacctatatt tattaccttc       360
tttctcgggt atttggctt tcagatcgga tttaaaaagc gggatgagct aatccactta        420
atgtcgatta cacggggctt tggcaaaaag aaggatgagg aagagagcga agccagaggt       480
agcaagttaa aaattctcga tacgagcgtt attattgatg gacgtattgc agatatatgc       540
aagaccgggt ttctcgaagg aactttggtc atccctggtt ttgtcctaga agagttacag       600
catattgccg actcgtctga tgtccttaaa agaaaccgtg gcagacgagg actcgatatt       660
ttaaataaga ttcagaaaga acttccgata aatgttgaaa tatatgaagg tgactttgag       720
gatattcaag aagtagacag caagctcgtg aagctagcga agtgacagaa aggtatggtc       780
gtcacaaatg actttaacct aaacaaagtc tgtgagttgc agggagtgca agtgttaaac       840
attaatgatt tagcgaatgc cgttaaacca gtcgtcctcc ctggagaaga gctcaatgtc       900
caagtgatta agatgggaaa agagcagaat caaggtgttg cctacttaga tgacggcaca       960
atgatcgtgg tagaaggtgg ccgtgattat atcgggaagc acgtagaagt cgtcgtgacg      1020
agcgtgctgc aaacgagtgc gggacggatg atttttgcca aacccaagct gttagaaaag      1080
gctttatag                                                             1089

<210> SEQ ID NO 31
<211> LENGTH: 5446
<212> TYPE: DNA
<213> ORGANISM: ARTIFICIAL
<220> FEATURE:
<223> OTHER INFORMATION: Commercial expression vector
```

<400> SEQUENCE: 31

```
gacggatcgg gagatctccc gatcccctat ggtcgactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
ttagggttag gcgttttgcg ctgcttcgcg atgtacgggc cagatatacg cgttgacatt     240
gattattgac tagttattaa tagtaatcaa ttacggggtc attagttcat agcccatata     300
tggagttccg cgttacataa cttacggtaa atggcccgcc tggctgaccg cccaacgacc     360
cccgcccatt gacgtcaata atgacgtatg ttcccatagt aacgccaata gggactttcc     420
attgacgtca atgggtggac tatttacggt aaactgccca cttggcagta catcaagtgt     480
atcatatgcc aagtacgccc cctattgacg tcaatgacgg taaatggccc gcctggcatt     540
atgcccagta catgacctta tgggactttc ctacttggca gtacatctac gtattagtca     600
tcgctattac catggtgatg cggttttggc agtacatcaa tgggcgtgga tagcggtttg     660
actcacgggg atttccaagt ctccacccca ttgacgtcaa tgggagtttg ttttggcacc     720
aaaatcaacg ggactttcca aaatgtcgta acaactccgc cccattgacg caaatgggcg     780
gtaggcgtgt acggtgggag gtctatataa gcagagctct ctggctaact agagaaccca     840
ctgcttactg gcttatcgaa attaatacga ctcactatag ggagacccaa gcttggtacc     900
gagctcggat ccactagtaa cggccgccag tgtgctggaa ttctgcagat atccatcaca     960
ctggcggccg ctcgagcatg catctagagg gccctattct atagtgtcac ctaaatgcta    1020
gagctcgctg atcagcctcg actgtgcctt ctagttgcca gccatctgtt gtttgcccct    1080
cccccgtgcc ttccttgacc ctggaaggtg ccactcccac tgtcctttcc taataaaatg    1140
aggaaattgc atcgcattgt ctgagtaggt gtcattctat tctggggggt ggggtggggc    1200
aggacagcaa gggggaggat tgggaagaca atagcaggca tgctggggat gcggtgggct    1260
ctatggcttc tgaggcggaa agaaccagct ggggctctag ggggtatccc cacgcgccct    1320
gtagcggcgc attaagcgcg gcgggtgtgg tggttacgcg cagcgtgacc gctacacttg    1380
ccagcgccct agcgcccgct cctttcgctt tcttcccttc ctttctcgcc acgttcgccg    1440
gctttccccg tcaagctcta aatcggggca tccctttagg gttccgattt agtgctttac    1500
ggcacctcga ccccaaaaaa cttgattagg gtgatggttc acgtagtggg ccatcgccct    1560
gatagacggt ttttcgccct ttgacgttgg agtccacgtt ctttaatagt ggactcttgt    1620
tccaaactgg aacaacactc aaccctatct cggtctattc ttttgattta agggattt     1680
tggggatttc ggcctattgg ttaaaaaatg agctgattta acaaaaattt aacgcgaatt    1740
aattctgtgg aatgtgtgtc agttagggtg tggaaagtcc ccaggctccc caggcaggca    1800
gaagtatgca aagcatgcat ctcaattagt cagcaaccag gtgtggaaag tccccaggct    1860
ccccagcagg cagaagtatg caaagcatgc atctcaatta gtcagcaacc atagtcccgc    1920
ccctaactcc gcccatcccg ccctaactc cgcccagttc cgcccattct ccgccccatg     1980
gctgactaat ttttttttatt tatgcagagg ccgaggccgc ctctgcctct gagctattcc    2040
agaagtagtg aggaggcttt tttggaggcc taggcttttg caaaaagctc ccgggagctt    2100
gtatatccat tttcggatct gatcaagaga caggatgagg atcgtttcgc atgattgaac    2160
aagatggatt gcacgcaggt tctccggccg cttgggtgga gaggctattc ggctatgact    2220
gggcacaaca gacaatcggc tgctctgatg ccgccgtgtt ccggctgtca gcgcagggc     2280
gcccggttct ttttgtcaag accgacctgt ccggtgccct gaatgaactg caggacgagg    2340
```

```
cagcgcggct atcgtggctg gccacgacgg gcgttccttg cgcagctgtg ctcgacgttg   2400
tcactgaagc gggaagggac tggctgctat tgggcgaagt gccggggcag gatctcctgt   2460
catctcacct tgctcctgcc gagaaagtat ccatcatggc tgatgcaatg cggcggctgc   2520
atacgcttga tccggctacc tgcccattcg accaccaagc gaaacatcgc atcgagcgag   2580
cacgtactcg gatggaagcc ggtcttgtcg atcaggatga tctggacgaa gagcatcagg   2640
ggctcgcgcc agccgaactg ttcgccaggc tcaaggcgcg catgcccgac ggcgaggatc   2700
tcgtcgtgac ccatggcgat gcctgcttgc cgaatatcat ggtggaaaat ggccgctttt   2760
ctggattcat cgactgtggc cggctgggtg tggcggaccg ctatcaggac atagcgttgg   2820
ctacccgtga tattgctgaa gagcttggcg gcgaatgggc tgaccgcttc ctcgtgcttt   2880
acggtatcgc cgctcccgat tcgcagcgca tcgccttcta tcgccttctt gacgagttct   2940
tctgagcggg actctggggt tcgaaatgac cgaccaagcg acgcccaacc tgccatcacg   3000
agatttcgat tccaccgccg ccttctatga aggttgggc ttcggaatcg ttttccggga   3060
cgccggctgg atgatcctcc agcgcgggga tctcatgctg gagttcttcg cccacccaa   3120 cttgtttatt gcagcttata atggttacaa ataaagcaat agcatcacaa atttcacaaa   3180
taaagcattt ttttcactgc attctagttg tggtttgtcc aaactcatca atgtatctta   3240
tcatgtctgt ataccgtcga cctctagcta gagcttggcg taatcatggt catagctgtt   3300
tcctgtgtga attgttatc cgctcacaat tccacacaac atacgagccg aagcataaa   3360 gtgtaaagcc tggggtgcct aatgagtgag ctaactcaca ttaattgcgt tgcgctcact   3420
gcccgctttc cagtcgggaa acctgtcgtg ccagctgcat taatgaatcg gccaacgcgc   3480
ggggagaggc ggtttgcgta ttgggcgctc ttccgcttcc tcgctcactg actcgctgcg   3540
ctcggtcgtt cggctgcggc gagcggtatc agctcactca aaggcggtaa tacggttatc   3600
cacagaatca ggggataacg caggaaagaa catgtgagca aaaggccagc aaaaggccag   3660
gaaccgtaaa aaggccgcgt tgctggcgtt tttccatagg ctccgccccc ctgacgagca   3720
tcacaaaaat cgacgctcaa gtcagaggtg gcgaaacccg acaggactat aaagatacca   3780
ggcgtttccc cctggaagct ccctcgtgcg ctctcctgtt ccgaccctgc cgcttaccgg   3840
atacctgtcc gcctttctcc cttcgggaag cgtggcgctt tctcaatgct cacgctgtag   3900
gtatctcagt tcggtgtagg tcgttcgctc caagctgggc tgtgtgcacg aaccccccgt   3960
tcagcccgac cgctgcgcct tatccggtaa ctatcgtctt gagtccaacc cggtaagaca   4020
cgacttatcg ccactggcag cagccactgg taacaggatt agcagagcga ggtatgtagg   4080
cggtgctaca gagttcttga agtggtggcc taactacggc tacactagaa ggacagtatt   4140
tggtatctgc gctctgctga gccagttacc ttcggaaaaa gagttggta gctcttgatc   4200 cggcaaacaa accaccgctg gtagcggtgg ttttttttgtt tgcaagcagc agattacgcg   4260
cagaaaaaaa ggatctcaag aagatccttt gatcttttct acgggtctg acgctcagtg   4320 gaacgaaaac tcacgttaag ggattttggt catgagatta tcaaaaagga tcttcaccta   4380 gatccttta aattaaaaat gaagttttaa atcaatctaa agtatatatg agtaaacttg   4440
gtctgacagt taccaatgct taatcagtga ggcacctatc tcagcgatct gtctatttcg   4500
ttcatccata gttgcctgac tccccgtcgt gtagataact acgatacggg agggcttacc   4560
atctggcccc agtgctgcaa tgataccgcg agacccacgc tcaccggctc agatttatc   4620 agcaataaac cagccagccg gaagggccga gcgcagaagt ggtcctgcaa ctttatccgc   4680
```

-continued

```
ctccatccag tctattaatt gttgccggga agctagagta agtagttcgc cagttaatag    4740
tttgcgcaac gttgttgcca ttgctacagg catcgtggtg tcacgctcgt cgtttggtat    4800
ggcttcattc agctccggtt cccaacgatc aaggcgagtt acatgatccc ccatgttgtg    4860
caaaaaagcg gttagctcct tcggtcctcc gatcgttgtc agaagtaagt tggccgcagt    4920
gttatcactc atggttatgg cagcactgca taattctctt actgtcatgc catccgtaag    4980
atgcttttct gtgactggtg agtactcaac caagtcattc tgagaatagt gtatgcggcg    5040
accgagttgc tcttgcccgg cgtcaatacg ggataatacc gcgccacata gcagaacttt    5100
aaaagtgctc atcattggaa aacgttcttc ggggcgaaaa ctctcaagga tcttaccgct    5160
gttgagatcc agttcgatgt aacccactcg tgcacccaac tgatcttcag catcttttac    5220
tttcaccagc gtttctgggt gagcaaaaac aggaaggcaa aatgccgcaa aaaagggaat    5280
aagggcgaca cggaaatgtt gaatactcat actcttcctt tttcaatatt attgaagcat    5340
ttatcagggt tattgtctca tgagcggata catatttgaa tgtatttaga aaaataaaca    5400 aatagggtt ccgcgcacat ttccccgaaa agtgccacct gacgtc                    5446
```

ENZYME REPLACEMENT THERAPY FOR TREATING LYSOSOMAL STORAGE DISEASES

This application is a 371 filing of International Patent Application PCT/IL2007/000152, filed Feb. 6, 2007, which claims the benefit of U.S. application No. 60/765,167 filed Feb. 6, 2006.

FIELD OF THE INVENTION

The present invention relates in general to the field of enzyme replacement therapy, and specifically to conjugates and fusion proteins of enzymes with polypeptide hormones. In particular, the polypeptide hormone is selected from leptin and granulocyte colony stimulating factor (G-CSF), which are able to cross the blood brain barrier, thereby transporting the required enzyme for the treatment of lysosomal storage diseases to the target tissue.

BACKGROUND OF THE INVENTION

Lysosomal Storage Diseases

Lysosomal Storage diseases (LSD) are inherited genetic defects, resulting in an enzyme deficiency. This deficiency prevents the lysosome from metabolizing cellular waste, and results in their accumulation in the cell. Excessive storage of proteins, saccharides and/or fats can cause permanent cellular and tissue damage, particularly in the brain, peripheral nervous system, liver, spleen, and bone marrow.

In some of the diseases the enzyme may be present but there are defects in its transport into the lysosome. There are currently more than 45 known conditions, which fall within the LSD category.

The diseases produce a variety of symptoms leading to progressive physical and/or mental deterioration over time. Some of the diseases may be present in a "mild" form, and others have a more severe impact on the patient. A number of patients survive into adulthood, but others with more severe symptoms may die in their teens or earlier.

Late-Onset Tay-Sachs Disease (LOTS), a LSD variant of Tay-Sachs, is much less common than the infantile form of the disease. As the name suggests, LOTS affects adults rather than infants, and manifests itself as a progressive loss of function of the nervous system. The enzyme defect, a deficiency or malfunction of the alpha subunit of β-hexosaminidase A (HEXA) resides in the same peptide as that of classical Tay-Sachs, but people with the late-onset condition have some minor residual β-hexosaminidase A activity rather than a complete absence of the active enzyme.

The onset of symptoms in LOTS patients is usually between adolescence and the mid-30's, with much variation among individuals. Neurological manifestations of the disease include muscle weakness, cramping, wasting, and twitching; lack of coordination; slurred speech; and dystonia. Some LOTS patients have reduced intellectual functions, which may involve memory impairment, difficulty with comprehension and deterioration in school performance. Behavioral alterations can include short attention span and changes in personality. About 40% of LOTS patients exhibit psychiatric symptoms such as psychotic episodes or depression.

For an effective treatment of LSDs, a therapeutic agent, such as the deficient enzyme, must be taken up by the affected cells and routed to the lysosome where it is able to act upon the harmful material residing therein.

Blood-Brain Barrier

The blood-brain barrier (BBB) tightly regulates the transport of molecules into the brain, such that hydrophilic molecules whose size exceeds a molecular weight of 300-500 are usually prevented from access to the central nervous system. The BBB is formed by the microvasculature of the brain and permeability is regulated by the capillary endothelial cell. Overall, there are three types of recognized BBB transport systems:

Carrier-mediated transport (CMT); Active efflux transport (AET); and Receptor-mediated transport (RMT).

RMT systems have been used to by pass the BBB, in what has been termed the "Trojan horse" approach: one compound, which is recognized by the BBB as "friendly" and permitted to pass into the brain or actively transported into the brain (the "Trojan horse") is conjugated or fused to a therapeutic molecule. This technique is useful for delivery of therapeutic proteins into the brain for the treatment of, for example, lysosomal storage disorders (LSD) and neurodegenerative diseases.

Certain therapeutic protein conjugates and/or fusion proteins are known in the art. US Patent Application Publication No. US 2005/0142141 relates to conjugates or fusion proteins composed of a therapeutic enzyme and a BBB targeting agent. The BBB targeting agent is referred to therein as a "molecular Trojan horse". According to that patent application, the BBB targeting agent is selected from transferrin, insulin, leptin, insulin-like growth factors, cationic peptides, lectins, or peptidomimetic monoclonal antibodies directed to the transferrin, insulin or leptin receptors. The invention is exemplified by a recombinant fusion protein comprising humanized murine monoclonal antibody to the insulin receptor fused to α-L-iduronidase and a conjugate of the rat anti-mouse transferrin receptor monoclonal antibody to the β-galactosidase.

PCT Publication No. WO 2003/057179 teaches conjugates composed of p97 (melanotransferrin) covalently linked to an enzyme associated with LSD.

Pan et al (2004) report that the 39 kDa receptor-associated protein (RAP) may provide a novel means of protein-based drug delivery to the brain.

PCT Publication No. WO 89/10134 relates to chimeric peptides for neuropeptide delivery through the blood-brain barrier. The chimeric peptides comprise a neuropeptide and a peptide exemplified by histone, capable of crossing the blood-brain barrier via receptor-mediated transcytosis. The neuropeptides act on extracellular receptors to exert their therapeutic effects and do not enter the neural cells.

U.S. Pat. No. 6,027,720 teaches a modified polypeptide having human G-CSF activity. The novel polypeptides differ from native G-CSF as a result of a substitution or deletion in the N-terminus domain of the protein.

U.S. Pat. Nos. 6,555,660 and 6,831,158 relate to a modified G-CSF polypeptide and to conjugates thereof with a non-polypeptide moiety. The novel polypeptides differ from native G-CSF in at least one amino acid residue, which is replaced by an amino acid having an attachment group for a polymer.

U.S. Pat. No. 6,518,235 relates to a method of improving memory in a patient comprising the administration of leptin.

There remains an unmet need for therapeutic agents, which are able to cross the blood brain barrier, for the treatment of lysosomal storage diseases and neurodegenerative disorders.

SUMMARY OF THE INVENTION

The present invention provides chimeric proteins comprising a polypeptide hormone covalently linked to a therapeutic enzyme for the treatment of a lysosome storage disease (LSD). The invention relates to the unexpected discovery that conjugates and fusion proteins comprising G-CSF or leptin are able to cross the blood brain barrier and are transported into their target cell, and in particular into the lysosome.

In one aspect the present invention provides a chimeric protein for the delivery of a therapeutic enzyme across the blood brain barrier, the chimeric protein comprising a protein hormone covalently linked to a therapeutic enzyme or active fragment thereof, wherein the peptide hormone is selected from a peptide hormone which is able to cross the blood brain barrier; and the therapeutic enzyme is an enzyme whose deficiency is linked to a lysosomal storage disease.

In one embodiment the present invention provides a chimeric protein for the delivery of a therapeutic enzyme across the blood brain barrier, the chimeric protein comprising a protein hormone covalently linked to a therapeutic enzyme or active fragment thereof, wherein the hormone is selected from the group consisting of G-CSF, leptin, variants thereof and fragments thereof; and the therapeutic enzyme is an enzyme whose deficiency is linked to a lysosomal storage disease. In some embodiment a therapeutic protein other than an enzyme associated with LSD is provided. In some embodiments the protein hormone is selected from the group consisting of leptin and a fragment thereof. The polypeptide sequences of human leptin precursor protein and human mature leptin are set forth in SEQ ID NO:1 and SEQ ID NO:2, respectively.

In other embodiments the protein hormone is selected from the group consisting of G-CSF and a fragment thereof. The polypeptide sequences of two human G-CSF precursor proteins having 207 amino acids and 204 amino acids are set forth in SEQ ID NO:5 and SEQ ID NO:9, respectively. The mature polypeptide sequences are set forth in SEQ ID NO:6 and SEQ ID NO:10, respectively.

In one embodiment the chimeric protein is capable of passing through the blood-brain barrier and entering a lysosome of a cell within the central nervous system.

In one embodiment the lysosomal storage disease is late onset Tay Sachs disease.

In one embodiment the enzyme is associated with a lysosomal storage disease. In another embodiment the enzyme is associated with late on-set Tay Sachs disease. In certain embodiments the enzyme is β-hexosaminidase A or a fragment thereof. In one embodiment the enzyme fragment is the β-hexosaminidase A α subunit (HEXA) or a fragment thereof. The polypeptide sequence of HEXA is set forth in SEQ ID NO:13. In specific embodiments an enzyme or enzyme fragment comprises amino acids 109-529 (SEQ ID NO:14); 1-191 (SEQ ID NO:15), and/or 403-529 (SEQ ID NO:16) of HEXA.

In one embodiment the chimeric protein is selected from the group consisting of a conjugate and a fusion protein.

In some embodiments the chimeric protein comprises a polypeptide having amino acid sequence set forth in any one of SEQ ID NO:1-2, 5-6 and 9-10; and a polypeptide sequence of a therapeutic enzyme whose deficiency is linked to a lysosomal storage disease. In certain preferred embodiments the therapeutic enzyme is HEXA or a fragment thereof, having amino acid sequence set forth in any one of SEQ ID NOS:13-16.

In various embodiments the chimeric protein is a protein conjugate or a fusion protein comprising a polypeptide having an amino acid sequence set forth in any one of SEQ ID NO:1-2, 5-6 and 9-10, and a polypeptide sequence of HEXA or a fragment thereof, having amino acid sequence set forth in any one of SEQ ID NOS:13-16.

In some embodiments the chimeric protein comprises an amino acid sequence set forth in any one of SEQ ID NOS:23-26.

In another embodiment the polypeptide hormone and the enzyme are linked by a linking group. In some embodiments the linking group comprises a disulfide bond. In other embodiments the linking group comprises one or more amino acids.

In a second aspect the present invention provides a polynucleotide sequence encoding the fusion protein according to the invention. Polynucleotide sequences of leptin precursor and mature leptin are set forth in SEQ ID NO:3 an SEQ ID NO:4, respectively. Polynucleotide sequences encoding the G-CSF 207 amino acid precursor and the G-CSF mature protein are set forth in SEQ ID NO:7 and SEQ ID NO:8, respectively. Polynucleotide sequences encoding the G-CSF 204 amino acid precursor and the G-CSF mature protein are set forth in SEQ ID NO:11 and SEQ ID NO:12, respectively.

Polynucleotide sequences encoding the HEXA precursor protein and fragments thereof are set forth in SEQ ID NO:17-20.

In another aspect the present invention provides a recombinant expression vector comprising a polynucleotide sequence encoding a fusion protein compromising a protein hormone and a therapeutic enzyme or active fragment thereof, wherein the protein hormone is wherein the protein hormone is able to cross the blood brain barrier; and the therapeutic protein is a protein whose deficiency is linked to a lysosomal storage disease. In some embodiments the protein hormone is selected from the group consisting of G-CSF, leptin, variants thereof and fragments thereof. The invention further provides a host cell comprising the recombinant expression vector.

In yet another aspect the present invention provides a pharmaceutical composition comprising as an active agent a) a chimeric protein comprising a protein hormone covalently linked to a therapeutic protein or fragment thereof, or b) a polypeptide encoding a chimeric protein comprising a protein hormone covalently linked to a therapeutic protein or fragment thereof; wherein the protein hormone is able to cross the blood brain barrier; and the therapeutic protein is a protein whose deficiency is linked to a lysosomal storage disease; and a pharmaceutically acceptable carrier or excipient. In some embodiments the protein hormone is selected from the group consisting of G-CSF, leptin, variants thereof and fragments thereof; and a pharmaceutically acceptable carrier or excipient.

In some embodiments the present invention provides a pharmaceutical composition comprising a recombinant expression vector of the present invention; and a pharmaceutically acceptable carrier or excipient.

Accordingly, the present invention provides a method of treating a lysosomal storage disease in a subject in need thereof comprising administering to the subject a pharmaceutical composition comprising a chimeric protein, wherein the chimeric protein comprises a protein hormone covalently linked to a therapeutic enzyme or fragment thereof, wherein the protein hormone is able to cross the blood brain barrier of the subject; and the therapeutic protein is a protein whose deficiency is linked to a lysosomal storage disease. In some embodiments the protein hormone is selected from the group consisting of G-CSF, leptin, variants thereof and fragments thereof.

In another aspect the present invention a method of treating a lysosomal storage disease in a subject in need thereof comprising administering to the subject a pharmaceutical composition comprising a recombinant expression vector comprising a polynucleotide encoding a protein hormone and a therapeutic enzyme or fragment thereof, wherein the protein hormone is able to cross the blood brain barrier of the subject; and the therapeutic enzyme is a protein whose deficiency is linked to a lysosomal storage disease. In some embodiments the protein hormone is selected from the group consisting of G-CSF, leptin, variants thereof and fragments thereof.

In one embodiment the subject is a mammal, preferably a human.

The present invention further provides the use of a chimeric protein comprising a protein hormone covalently linked to a therapeutic protein or fragment thereof, wherein the wherein the protein hormone is able to cross the blood brain barrier of the subject; and the therapeutic enzyme is a protein whose deficiency is linked to a lysosomal storage disease for the preparation of a medicament for the treatment of a lysosomal storage disease. In some embodiments the protein hormone is selected from the group consisting of G-CSF, leptin, variants thereof and fragments thereof.

The present invention further provides the use of a polynucleotide encoding a fusion protein wherein the fusion protein comprises a protein hormone and a therapeutic enzyme or fragment thereof, wherein the protein hormone is selected from the group consisting of G-CSF, leptin, variants thereof and fragments thereof; and the therapeutic enzyme is a protein whose deficiency is linked to a lysosomal storage disease, for the preparation of a medicament for the treatment of a lysosomal storage disease.

The present invention explicitly excludes known conjugates.

These and other aspects of the present invention will be apparent from the description, figures and claims that follow.

BRIEF DESCRIPTION OF THE FIGURES

FIG. 5A-5B illustrate detection of CAT in mouse brain homogenates from G-CSF/CAT injected mice using western blotting with anti-CAT antibody. The conjugate was injected intravenously.

FIG. 6A-6C depict immunofluorescence detection of CAT in the mouse brain, following peripheral injection of a G-CSF/CAT conjugate, using anti-CAT antibodies as the primary antibody and FITC-goat anti-rabbit IgG (H+L) conjugate as the secondary antibody. Brain slices from control (6 Å) and G-CSF/CAT conjugate-treated mice (6B and 6C) are shown, and staining represents CAT within the brain.

FIGS. 7A-7B demonstrate positive staining to anti-CAT following peripheral G-CSF-CAT injection; FIG. 7C shows the same region from a control mouse.

DETAILED DESCRIPTION OF THE INVENTION

Figure 1:
FIG. 1 depicts RT-PCR products using primers specific for the mouse G-CSF Receptor (G-CSFR). G-CSFR mRNA was detected in aortic homogenates, peritoneal macrophages and brain tissue.

The present invention relates to chimeric proteins, pharmaceutical compositions comprising chimeric proteins, methods of producing a chimeric protein and methods of using the protein. Specifically, the present invention generally provides compositions and methods for enhanced delivery of lysosomal storage disease related agents to the lysosomes of cells affected by a lysosomal storage disease. The invention relates to the unexpected discovery that G-CSF and leptin and variants thereof not only cross the blood brain barrier (BBB) but also are transported into lysosomes.

Without wishing to be bound to theory, crossing the BBB depends on the binding of the G-CSF or leptin conjugated molecules to the ligand-binding domain of the respective receptor for each of these molecules, followed by selective entry through unique biological transport routes allowing the access of the native molecule to the brain. In this invention, the therapeutic chimeric protein is carried through the BBB by G-CSF or leptin to which they are attached. The entire conjugate will be transported through the BBB using the routes allowing G-CSF or leptin entry.

Definitions

For convenience and clarity certain terms employed in the specification, examples and claims are described herein.

"G-CSF" refers to granulocyte colony stimulating factor and to analogs, which are functional equivalents thereof, i.e. a polypeptide having greater than about 75%, 80%, 90% or 95% homology of their corresponding amino acid sequences which is able to bind to the G-CSF receptor and undergo internalization.

"Leptin" includes analogs of leptin, which are functional equivalents, i.e. a polypeptide having greater than about 75%, 80%, 90% or 95% homology of their corresponding amino acid sequences which is able to bind to the OB receptor and undergo internalization into a cell.

Fragments of leptin and G-CSF, which are able to bind their respective receptors and undergo internalization, are encompassed in the present invention.

Functional equivalents include allelic variants of leptin and G-CSF, and human, and non-human i.e. ovine, murine, chicken, rat and/or rabbit leptin or G-CSF, and derivatives thereof. Leptin or G-CSF can be in the form of acidic or basic salts, or in its neutral form. In addition, individual amino acid residues can be modified, such as by oxidation or reduction. Moreover, various substitutions, deletions, or additions can be made to the amino acid or nucleic acid sequences, the net effect of which is to retain or improve upon the desired biological activity of leptin or G-CSF. Due to code degeneracy, for example, there may be considerable variation in nucleotide sequences encoding the same amino acid sequence.

As used herein the terms covalently "linked" or "bound" or "attached" refer to molecules that are in contact with one another via a covalent bond. A peptide bond is a covalent bond.

A "chimeric protein" as used herein refers to a modified protein, particularly a protein comprising a hormone selected from G-CSF and leptin and at least one therapeutic enzyme or other therapeutic protein introduced therein. The chimeric protein comprises a hormone fused or covalently linked to at least one therapeutic protein moiety.

As used herein, a "conjugate" refers to the product of conjugation between one or more of (a) a hormone selected from leptin and G-CSF and (b) a therapeutic enzyme. Conjugation as used herein involves covalent interactions. Accordingly, where reference is made to "comprising," "conjugation," "coupling," etc, these references should be taken to include a covalent interaction between the therapeutic protein to be delivered and the leptin or G-CSF carrier molecule, in such a manner as to allow delivery of the therapeutic protein to the brain. The conjugate may be prepared by, inter alia, chemical conjugation sand may involve direct or indirect (i.e. via a linker) conjugation.

As used herein, the term "fusion protein" refers to the combination of heterologous amino acid sequences in one polypeptide chain by in-frame combination of their coding nucleotide sequences. The amino acid sequences of the hormone and enzyme may be directly combined or may have a peptide linker or spacer between them. Without wishing to be bound to theory a linker or spacer may make it more likely that the proteins fold independently. A fusion protein is generally prepared using recombinant DNA technique, known to those with skill in the art.

The term "heterologous sequences" refers to amino acid sequences that are not identical sequences. Heterologous sequences can originate from the same organism, i.e. human leptin and human HEXA or human G-CSF and human HEXA.

The alpha subunit of β-hexosaminidase A or "HEXA" refers to the enzyme that which, when deficient, causes Tay-Sachs disease, a progressive fatal neurological disorder concentrated in people of European Jewish (Ashkenazi) descent.

As used herein "treatment" in a subject is intended to include prophylaxis and treating, alleviating or palliating a disorder, and thus providing relief from the symptoms associated with those disorders.

The terms "Lysosomal Storage Disease" or "LSD" as used herein refer to a family of inherited diseases related to an enzyme deficiency. The deficiency results in detrimental accumulation of metabolic products in the lysosome. Representative LSDs include aspartylglucosaminuria, cholesteryl ester storage disease; cystinosis; Danon disease; Fabry disease; Farber's disease; fucosidosis; falactosialidosis types I/II; Gaucher disease types 1, 2, 3; globoid cell leucodystrophy/Krabbe disease; glycogen storage disease II/Pompe disease; GM1-gangliosidosis types I/III; GM2-gangliosidosis type I/Tay-Sachs disease; GM2-gangliosidosis type II/Sandhoff disease; α.-mannosidosis types I/II; β-mannosidosis; metachromatic leukodystrophy (MLD); mucolipidosis type I/sialidosis types I/II; mucolipidosis types II/III; mucolipidosis type III pseudo-Hurler polydystrophy; mucopolysaccharidosis (e.g. types I, II, IIIA, IIIB, IIIC, IIID, IVA, IVB, VI, VII, IX); multiple sulphatase deficiency; neuronal ceroid lipofuscinosis (e.g. Batten, infantile, late infantile and adult); Niemann-Pick disease (e.g. types A, B, C1, C2); Schindler disease types I/II; sialic acid storage disease; Wolman's disease (acid lipase deficiency).

Accordingly the therapeutic protein is selected from the group consisting of aspartylglucosaminidase, acid lipase, cysteine transporter, Lamp-2, α-galactosidase A, ceramidase, α-L-fucosidase, β-hexosaminidase A, GM2 ganglioside activator protein, α-D-mannosidase, β-D-mannosidase, arylsulphatase A, saposin B, neuraminidase, α-N-acetylglucosaminidase phosphotransferase, phosphotransferase γ-subunit, L-iduronidase, iduronate-2-sulphatase, heparan-N-sulphatase, α-N-acetylglucosaminidase, acetylCoA: N-acetyltransferase, N-acetylglucosamine 6-sulphatase, galactose 6-sulphatase, β-galactosidase, N-acetylgalactosamine 4-sulphatase, hyalurono-glucosaminidase, multiple sulphatases, palmitoyl protein thioesterase, tripeptidyl peptidase I, acid sphingomyelinase, α-galactosidase B, sialic acid transporter and fragments thereof. A fragment thereof includes an active fragment that is able to degrade or assist in the degradation of GM2 ganglioside. The enzyme can further be a chimeric enzyme; for example, the beta subunit of β-hexosaminidase A wherein certain active sequences from the alpha subunit are substituted. The polypeptide and polynucleotide sequences of the beta subunit of human β-hexosaminidase A are set forth in SEQ ID NO:21 and SEQ ID NO:22, respectively.

In some embodiments the protein is an enzyme. In certain embodiments the enzyme is β-hexosaminidase A or a fragment thereof.

Lysosomal deficiency diseases and the associated protein deficiencies include the following:

Glycogen storage disease type II: alpha-glucosidase deficiency;

Mucopolysaccharidoses (MPS)

MPS type IH, Hurler syndrome: alpha-L-iduronidase deficiency;

MPS type I H/S, Hurler-Scheie syndrome: alpha-L-iduronidase deficiency;

MPS type I S, Scheie syndrome: alpha-L-iduronidase deficiency;

MPS type II A and B, Hunter syndrome: iduronate sulfatase deficiency;

MPS type III A-D, Sanfilippo syndrome: heparan N-sulfatase deficiency;

MPS type IV A, Morquio syndrome: galactose 6-sulfatase deficiency;

MPS type VI, Maroteaux-Lamy syndrome: arylsulfatase B deficiency;

MPS type VII, Sly syndrome: beta-glucuronidase deficiency;

Mucolipidosis II (1-cell disease) and mucolipidosis III: phosphotransferase deficiency;

Schindler disease/Kanzaki disease: alpha-N-acetylgalactosaminidase deficiency;

Danon Disease: LAMP-2 deficiency;

Glycoprotein Degradation Disorders including Alpha-mannosidosis and beta-mannosidosis; Fucosidosis; Sialidosis: alpha-N-acetyl neuraminidase deficiency (sialidase); and Aspartylglucosaminuria (AGU): aspartylglucosaminidase (AGA) deficiency;

Carbohydrate-deficient glycoprotein syndrome: N-acetylaspartate deficiency;

Wolman and cholesterol ester storage disease: acid lipase deficiency;

Farber disease, disseminated lipogranulomatosis: acid ceramidase deficiency;

Niemann-Pick disease type A and B: sphingomyelinase deficiency;

Niemann-Pick disease C1: NPC1 deficiency; Niemann-Pick disease C2;

Gaucher disease types I, II, and III: beta-glucosidase deficiency;

Krabbe disease, infantile globoid-cell leukodystrophy: galactosylceramidase deficiency; Fabry disease: alpha-galactosidase A deficiency; Multiple sulfatase deficiency: sulfatases deficiency; GM1 gangliosidosis and Morquio B disease: beta-galactosidase deficiency;

GM2 gangliosidosis, Tay-Sachs, late onset Tay Sachs and Sandhoff diseases: (3-hexosaminidase deficiency; Cystinosis: cysteine transporter deficiency;

Sialic acid storage disease: sialic acid transporter deficiency;

Metachromatic leukodystrophy: galactose-3-sulfatase deficiency; Galactosialidosis (neuraminidase, beta-galactosidase or protective protein/cathepsin A (PPCA) deficiency;

Neuronal ceroid lipofuscinosis, infantile: palmityl protein thioesterase deficiency; Neuronal ceroid lipofuscinosis, late infantile: carboxypeptidase deficiency.

Physiological Transport of Hormones to the Brain: Granulocyte-Colony Stimulating Factor (G-CSF) and Leptin Overall, there are three types of recognized BBB transport systems:

a) Carrier-mediated transporters (CMT) such as the Glut1 glucose transporter, the LAT1 large neutral amino acid transporter, the CNT2 adenosine transporter, adenine or nucleobase transporter, the choline transporter and the BBB thyroid hormone transporter; b) Active efflux transporters (AET) include p-glycoprotein, organic anion transporting polypeptide type 2 (oatp2) and BBB-specific anion transporter type 1 (BSAT1); and c) Receptor-mediated transporters (RMT), such as the transferrin receptor.

Leptin

The discovery of leptin and the understanding of its action within specific brain centers provide evidence for a BBB-dependent hormonal link between the adipocyte and the brain. Leptin is a 16-kDa protein mainly secreted by the adipocyte, which circulates, in part, while linked to binding proteins and crosses the blood-brain barrier (BBB) to interact with its receptors at the arcuate nucleus, where it curbs appetite and modulates energy balance. The brain targets for leptin action are within the areas presumably protected by the BBB.

Leptin is recognized by the leptin receptor (OB-R), which is a product of the db gene. Different OB-R isoforms have been found which are generated by differential splicing and are widely distributed in many organs. The short form (OB-Ra) of the leptin receptor, which has truncated intracellular amino acid sequences and thus, little intracellular signaling capacity, is the characteristic isoform present in the choroid plexus and serves as a transporter. In contrast, in the hypothalamus, where specific receptor-activated, leptin dependent function must take place for normal feeding behavior, the OB-R appears to have a long intracellular domain (long form or OB-Rb) that contains putative motifs for janus protein-tyrosine kinase (JAK) and signal transducers and activators of transcription (STATs).

The delivery of leptin into the central nervous system (CNS) seems to represent a crucial step toward the regulation of food intake and energy balance. Different studies have shown the presence of specific OB-Ra in the brain capillaries as well as binding of $^{125}$I-leptin to human and mouse brain capillaries, which constitute the blood-brain barrier. The presence of the OB-Ra and, to a lesser extent, OB-Rb in the endothelium of the human brain has been recently confirmed (Burguera et al., 2000). The presence of a specific OB-Ra in the endothelial cells would allow leptin to gain access through the capillary wall to the brain.

Human leptin is expressed as precursor polypeptide consisting of 167 amino acid residues. A signal peptide consisting of 21 amino acid residues at the amino terminus is cleaved, and 146 amino acid mature protein is secreted. Human precursor polypeptide (NCBI accession number BAA09787) has an amino acid sequence set forth in SEQ ID NO:1. The polypeptide sequence of mature leptin is set forth in SEQ ID NO:2. The corresponding polynucleotide sequence of the leptin precursor is set forth in SEQ ID NO:3 The polynucleotide sequence of mature leptin is set forth in SEQ ID NO:4

Granulocyte Colony Stimulating Factor

G-CSF is a 19.6-kDa glycoprotein commonly used to treat neutropenia. Known sources of G-CSF in the body include monocytes, mesothelial cells, fibroblasts, and endothelial cells G-CSF stimulates the growth of neutrophil granulocyte precursors and regulates survival of mature neutrophils by inhibition of apoptosis.

It was recently shown that G-CSF passes the intact blood-brain barrier and reduces infarct volume in two different rat models of acute stroke. G-CSF is also known to display strong antiapoptotic activity in mature neurons and activate multiple cell survival pathways. G-CSF has not been shown to be useful as a carrier molecule to the transport of therapeutic agents into the brain.

Receptors for G-CSF are present on precursors and mature neutrophilic granulocytes, monocytes, platelets, and endothelial cells. Recently it was found that G-CSF and its receptor are not only widely expressed by neurons in the CNS, but their expression is induced by ischemia. Surprisingly, the G-CSF receptor was also expressed by adult neural stem cells, and G-CSF induced neuronal differentiation in vitro (Schabitz, et al., 2003).

The G-CSF receptor (G-CSFR) is a type I membrane protein that belongs to the hemopoietic growth factor receptor super family. The membrane-proximal half of the G-CSFR cytoplasmic region is sufficient for transducing the proliferation signal, whereas its membrane-distal half of the cytoplasmic region is essential for the differentiation signal. G-CSFR activates Janus family kinases (JAKs), specifically JAK1 and JAK2, and STAT protein, which translocates to the nucleus and subsequently regulates gene expression. STAT3 is the principal STAT protein activated by G-CSFR.

In hematopoietic and neuronal cells, G-CSF activates intracellular signaling pathways via the STAT3 and the PI3K/Akt and ERK5 pathways, which are linked to suppression of apoptosis and proliferation.

Human G-CSF is expressed as precursor polypeptide consisting of 207 amino acid residues (SEQ ID NO:5) or 204 amino acid residues (SEQ ID NO:9). A signal peptide consisting of 30 amino acid residues at the amino terminus is cleaved, and 177 or 174 amino acid mature protein is secreted (SEQ ID NO:6; SEQ ID NO:10, respectively).

Table 1 provides a list of the polypeptide and polynucleotide sequences disclosed herein.

TABLE 1

| SEQ ID NO: | Sequence name: | Accession number |
|---|---|---|
| 1 | Human leptin precursor protein | BAA09787 |
| 2 | Human mature leptin | BAA09787 |
| 3 | Human leptin precursor polynucleotide | D63519 |
| 4 | Human mature leptin polynucleotide | D63519 |
| 5 | Human G-CSF precursor protein (1-207) | CAA27291 |
| 6 | Human G-CSF protein (31-207) | CAA27291 |
| 7 | Human G-CSF precursor polynucleotide | XO3656 |

TABLE 1-continued

| SEQ ID NO: | Sequence name: | Accession number |
|---|---|---|
| 8 | Human G-CSF protein polynucleotide (31-207) | XO3656 |
| 9 | Human G-CSF precursor protein | CAA27290 |
| 10 | Human G-CSF protein (31-204) | CAA27290 |
| 11 | Human G-CSF polynucleotide | XO3655 |
| 12 | Human G-CSF (31-204) polynucleotide | XO3655 |
| 13 | Human HEXA (β-hexosaminidase A α subunit) precursor protein (1-529) | NP_000511 |
| 14 | Human HEXA protein (109-529) | NP_000511 |
| 15 | Human HEXA protein fragment (1-191) | NP_000511 |
| 16 | Human HEXA protein fragment (403-529) | NP_000511 |
| 17 | Human HEXA precursor protein (1-529) polynucleotide | NM_000520 |
| 18 | Human HEXA fragment (109-529) polynucleotide | NM_000520 |
| 19 | Human HEXA fragment (1-191) polynucleotide | NM_000520 |
| 20 | Human HEXA fragment (403-529) polynucleotide | NM_000520 |
| 21 | Human β-hexosaminidase A β subunit precursor protein (1-529) | NP_000512 |
| 22 | Human β-hexosaminidase A β subunit precursor (1-529) polynucleotide | NM_000521 |
| 23 | Conjugate GCSF-HEXA (1-529) | |
| 24 | Conjugate GCSF-HEXA fragment (109-529) | |
| 25 | Conjugate GCSF-HEXA fragment (1-191) | |
| 26 | Conjugate Leptin-HEXA (1-529) | |
| 27 | CAT protein | M55620 |
| 28 | CAT polynucleotide | |
| 29 | β-gal protein | BAB05741 |
| 30 | β-gal polynucleotide | BA000004 |
| 31 | pcDNA3 polynucleotide | |

Chimeric Proteins

The chimeric proteins of the present invention may be produced by chemical synthetic methods, by chemical linkage between the two moieties, or by fusion of a coding sequence of a targeting moiety and a coding sequence of a therapeutic protein under the control of a regulatory sequence, which directs the expression of the fusion polynucleotide in an appropriate host cell Conjugation of Hormone to Enzyme The protein hormone, including G-CSF or leptin, and the enzyme are conjugated directly or indirectly to each other (i.e., through an extended linker). Linker compounds can also be used to effect the coupling; both homobifunctional and heterobifunctional linkers are available from Pierce Chemical Company, Rockford, Ill., USA. In general, G-CSF or leptin conjugates may be prepared using techniques well known in the art. There are numerous approaches for the conjugation or chemical crosslinking of agents to a polypeptide such as leptin or G-CSF, and one skilled in the art can determine which method is most appropriate for conjugating a particular enzyme. The method employed must be capable of joining the enzyme and the leptin or G-CSF without interfering with the ability of leptin or G-CSF to bind to its respective receptor, preferably without significantly altering the desired activity of the enzyme or peptide once delivered. Preferred methods of conjugating leptin or G-CSF to various enzymes are described in the examples section, supra. Such attachment can be any suitable chemical linkage, direct or indirect, as by means of a peptide bond or via covalent bonding to an intervening linker element, such as a linker peptide or other chemical moiety, such as an organic polymer. Such chimeric peptides may be linked via bonding at the carboxy (C) or amino (N) termini of the peptides, or via bonding to internal chemical groups such as straight, branched, or cyclic side chains, internal carbon or nitrogen atoms, and the like.

Methods of crosslinking proteins and peptides are well known to those of skill in the art. A plurality of crosslinkers is commercially available for conjugating a two or more peptide or polypeptide sequences. The crosslinker is generally chosen based on the reactive functional groups available or inserted on the therapeutic agent, in this case an enzyme. In addition, a photoreactive crosslinker can be used.

In other instances, it may be desirable to include a spacer between the protein hormone and the enzyme, enzyme subunit or peptide. When a linker is used, the linker is preferably an organic moiety constructed to contain an alkyl, aryl and/or amino acid backbone, and containing an amide, ether, ester, hydrazone, disulphide linkage or any combination thereof. Preferred linkers are those containing esters or hydrazones that are stable at physiological pH, but hydrolyze to release the enzyme when exposed to lysosomal pH. Disulphide linkages are preferred because they are sensitive to reductive cleavage. In addition, amino acid linkers may be designed to be sensitive to cleavage by specific enzymes in the desired target organ or more preferably, the lysosome itself.

In some embodiments the linker comprises a disulfide bond. For conjugation purposes, cross-linkers various will be used, based on S—S (disulfide) groups, such that once the conjugates enter the brain, the S—S bond will be reduced to an SH group thus releasing the enzyme intracellularly at the target cell within the brain territory.

Enzymes, hormones and fragments thereof may be produced by recombinant methods, as detailed below, or by direct peptide synthesis using solid-phase techniques. (See, e.g., Creighton, 1984). Protein synthesis may be performed by manual techniques or by automation. Automated synthesis may be achieved, for example, using the Applied Biosystems 431A peptide synthesizer (Perkin Elmer).

Fusion Proteins

In some embodiments of the present invention, the leptin-enzyme or leptin-enzyme subunit or G-CSF-enzyme or G-CSF-enzyme subunit conjugate is a leptin-enzyme (or enzyme subunit) or G-CSF-enzyme (or enzyme subunit) fusion protein. Fusion proteins may be prepared using standard techniques known in the art. Typically, a DNA molecule encoding leptin or G-CSF or an equivalent thereof is linked to a DNA molecule encoding the enzyme or an enzyme subunit. The chimeric DNA construct, along with suitable regulatory elements can be cloned into an expression vector and expressed in a suitable host. The resultant fusion proteins contain leptin or G-CSF fused to the selected enzyme.

Accordingly, the present invention further encompasses the recombinant DNA, a recombinant expression vector comprising the recombinant DNA and a host cell comprising the recombinant expression vector.

Recombinant methods for designing, expressing and purifying fusion proteins are known in the art (see, e.g. Sambrook et al., 1992). Nucleic acid molecules according to the invention may include DNA, RNA, or derivatives of either DNA or RNA. An isolated nucleic acid sequence encoding an enzyme, an enzyme subunit or hormone can be obtained from its natural source, either as an entire (i.e., complete) gene or a portion thereof. A nucleic acid molecule can also be produced using recombinant DNA technology (e.g., polymerase chain reaction (PCR) amplification, cloning) or chemical synthesis. Nucleic acid sequences include natural nucleic acid sequences and homologs thereof, including, but not limited to, natural allelic variants and modified nucleic acid sequences in which nucleotides have been inserted, deleted, substituted, and/or inverted in such a manner that such modifications do not substantially interfere with the nucleic acid molecule's ability to encode a functional peptide of the present invention.

A polynucleotide or oligonucleotide sequence can be deduced from the genetic code of a protein, however, the degeneracy of the code must be taken into account, as well as the allowance of exceptions to classical base pairing in the third position of the codon, as given by the so-called "Wobble rules". Moreover, polynucleotides that include more or less nucleotides can result in the same or equivalent proteins.

The present invention includes a nucleic acid sequence of the present invention operably linked to one or more transcription control sequences to form a recombinant construct. The phrase "operably linked" refers to linking a nucleic acid sequence to a transcription control sequence in a manner such that the molecule is able to be expressed when transfected (i.e., transformed, transduced or transfected) into a host cell. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. Preferred transcription control sequences include those which function in animal, bacteria, helminth, insect cells, and animal cells.

In order to express a biologically active fusion protein of the invention, the nucleotide sequences encoding said fusion proteins according to the present invention may be inserted into appropriate expression vector, i.e., a vector which contains the necessary elements for the transcription and translation of the inserted coding sequence. Thus, for example, a polynucleotide encoding the fusion peptide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

Vectors can be introduced into cells or tissues by any one of a variety of known methods within the art, including in vitro recombinant DNA techniques, synthetic techniques, and in vivo genetic recombination. Such methods are generally described in Sambrook et al., 1992, and include, for example, stable or transient transfection, lipofection, electroporation and infection with recombinant viral vectors.

A variety of expression vector/host systems may be utilized to contain and express sequences encoding the fusion proteins of the invention. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems. The invention is not limited by the host cell employed. The expression of the construct according to the present invention within the host cell may be transient or it may be stably integrated in the genome thereof.

Depending on the vector system and host utilized, any number of suitable transcription and translation elements, including constitutive and inducible promoters, may be used. For example, when cloning in bacterial systems, inducible promoters such as the hybrid lacZ promoter of the Bluescript® phagemid (Stratagene, LaJolla, Calif.) or pSport1™ plasmid (Gibco BRL) and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable.

Late Onset Tay-Sachs Disease

Tay-Sachs disease is one of the entities comprising a subgroup of the lysosomal storage diseases, the $G_{M2}$-gangliosidoses, which all result from a failure in lysosomal degradation of a molecule known as "$G_{M2}$-ganglioside" (Mahuran, 1991). In Tay Sachs disease, the enzyme responsible for the breakdown of $G_{M2}$-ganglioside, 3-hexosaminidase, is defective due to a mutation in one of the subunits making up the enzyme molecule, the α chain (HEXA) (Mahuran, 1999). This genetically transmitted structural defect leads to functional decline in β-hexosaminidase A enzyme activity. Since the highest concentration of gangliosides is found in the central nervous system, the absence of normal β-hexosaminidase, the enzyme responsible for $G_{M2}$-ganglioside degradation, is particularly detrimental to the brain and spinal cord. The classic infantile form of Tay Sachs disease, which results from very severe β-hexosaminidase A deficiency, usually leads to death between 3 and 5 years of life. Patients with LOTS, on the other hand, in whom there is some residual activity of β-hexosaminidase A (2-3% of the normal range), manifest in late childhood, in their teens or, occasionally, much later, with signs of cerebellar damage such as impaired speech (dysarthria), abnormal gait (ataxia) and anterior horn cell malfunction, leading to proximal limb weakness and muscle atrophy. In some patients, clinical presentation and disease course may be dominated by neuropsychiatric problems such as psychotic episodes, bipolar disorder or depression (Navon, 2001; Neudorfer, et al., 2005).

LOTS is a rare disorder encountered mainly, but not exclusively, in Jews of Eastern-European extraction. Several dozens of patients have been thus far reported in the literature. Left untreated, individuals with LOTS experience a relentless downhill course characterized by gradual loss of motor and cognitive function often aggravated by psychiatric crises: they deteriorate from an apparently normal young person to a severely crippled individual who is difficult to communicate with and unable to move around or perform simple daily routine tasks without the help of others.

The lysosomal enzyme β-hexosaminidase A (together with the cofactor GM2 activator protein), catalyzes the degradation of the ganglioside GM2, and other molecules containing terminal N-acetyl hexosamines. β-hexosaminidase A is composed of two subunits, alpha and beta, which are encoded by separate genes. Hexosaminidase A (HEXA) is the alpha subunit of β-hexosaminidase A. Both β-hexosaminidase A alpha and beta subunits are members of family 20 of glycosyl hydrolases. Mutations in the alpha or beta subunit genes lead to an accumulation of GM2 ganglioside in neurons and the resulting neurodegenerative disorders termed the GM2 gangliosidoses. Alpha subunit gene mutations lead to Tay-Sachs disease (GM2-gangliosidosis type I).

The HEXA gene (alpha-chain gene; Gene map locus 15q23-q24) is about 35 kb long and contains 14 exons. Myerovitz et al (1985) cloned the alpha chain from an adult human liver library and found an open reading frame corresponding to 529 amino acids, with a molecular weight of approximately 60 kD. The first 17 to 22 amino acids appear to represent a signal sequence.

One key feature of the function alpha and beta subunits, is their distinct substrate specificity. Indeed, well-defined domains in human hexosaminidase confer distinctive substrate specificity to Hex-A (alpha-beta), Hex-B (beta-beta), and Hex-S (alpha-alpha) isozymes. The active site on the beta subunit primarily degrades neutral substrates, whereas the alpha-subunit site confers activity against sulfated substrates. Only Hex-A, together with the GM2 activator protein, can degrade GM2 ganglioside. Through the generation of chimeric hexosaminidase subunits, which included interchanging analogous regions of the alpha and beta subunits, Pennybacker et al (1996) identified the amino acid sequences required for each enzymatic activity profile. Of critical importance for the present proposal, these experiments were based on chimeric constructs produced in the baculovirus expression system expressed in HeLa cells. To degrade GM2 ganglioside in the presence of GM2 activator protein, two noncontiguous sequences in the alpha subunit (amino acids 1-191 and 403-529) were found to be critical. When these sequences were substituted into analogous positions in the beta subunit, they conferred activity against the sulfated substrate, just as would be expected by native alpha subunit per se. Amino acids 225-556 in the beta subunit are required for activator-dependent GM2 ganglioside degradation by HexA. One study showed that alpha-chain alone secreted to culture medium could be taken up by HexA-(HEXA) deficient cells, which was followed by restoration of intracellular HexA activity (Guidotti, et al., 1998).

On way to overcome the progressively detrimental sequence of cellular events induced by lysosomal enzyme deficiency, is to administer a synthetic, fully functioning enzyme to replace the defective enzyme. There is some crucial observation in this respect. Even a very small increase in intracellular enzyme activity (1-5%) achieved correction of the excessive storage. Only a low level of HexA activity is needed to ameliorate the clinical phenotype in Tay Sachs disease and asymptomatic individuals have been identified with residual activities of ≥10% of normal. There is also evidence that 5-10% of normal HexA levels represents a "critical threshold" for disease (Conzelmann, et al., 1983).

Under experimental conditions, utilization of molecular biology-based strategies appears to offer much better opportunity for enzyme replacement therapy in Tay Sachs disease. There is evidence for successful induction of β-hexosaminidase A synthesis in human fibroblasts obtained from patients suffering from Tay Sachs disease. In one study, a human β-hexosaminidase A cDNA was first subcloned into the adenoviral plasmid pAdRSV. Hexa replication-deficient adenovirus was generated by homologous recombination in 293 cells. Tay Sachs fibroblasts were then infected with the adenoviral plasmid containing the human β-hexosaminidase A cDNA. This resulted in a 25-fold rise in secreted β-hexosaminidase A. Indeed, the Tay Sachs fibroblasts expressing the recombinant normal α-chain of β-hexosaminidase A had an enzyme activity ranging from 40 to 84% of the level seen in normal cells. Further, the enzyme encoded by the adenovirus was shown to be correctly transported into the lysosomes and to normalize the impaired degradation of GM2 ganglioside in the formerly β-hexosaminidase A deficient cells (Akli, et al., 1996).

Another study not only demonstrated that progenitor neural cell lines transfected with ectopic retroviruses encoding the human β-hexosaminidase A α-subunit cDNA could stably express and secrete high levels of biologically active β-hexosaminidase A, but that these genetically engineered cells, once transplanted into the brains of fetal and newborn mice, produced substantial amounts of enzymatically active human β-hexosaminidase A (Lacorazza et al., 1996). Hence, the production of human β-hexosaminidase A can be induced by transfecting human cells with the human β-hexosaminidase A alpha gene. This information comprises reasonable "proof of concept" for two critical aspects of any potential future enzyme replacement therapy for Tay Sachs disease: first, ezymatically active β-hexosaminidase A alpha subunit can be generated using well-established molecular biology techniques; second, human HEXA deficient Tay Sachs cells are capable of proper utilization of HEXA, at least when generated within the cell itself.

Enzyme replacement therapy has been successfully implemented in several lysosomal storage diseases, each characterized by a deficiency in the structure and activity of a specific lysosomal enzyme: Gaucher's (type 1) disease, Fabry's disease, Pompe's disease, Hurler's disease and Maroteaux-Lamy syndrome (Brady, et al., 2004). The feasibility of the enzyme replacement approach in the treatment of such disorders is best exemplified in type 1 Gaucher's disease, where cumulative widespread experience with replacement therapy with mannose-terminated glucocerebrosidase clearly indicates that many of the clinical manifestations of Gaucher's disease can be either reversed or at least ameliorated. Indeed, experience with enzyme replacement therapy in that disease has been so extensive that specific recommendations for both initial treatment and subsequent dose adjustments now exist, based on a schedule of regular assessment and monitoring, and achievement and maintenance of defined therapeutic goals.

In the examples discussed above, enzyme delivery to patients can be relatively easily accomplished through direct injection of the enzyme. Once the enzyme circulates in the blood, various cell types in all organs receiving normal blood supply take it up. The situation is far more complex when cells in the greatest need of normal enzyme activity reside within the brain, since the brain is tightly protected from entry of "foreign" or large molecules" by the BBB. Therefore, neurological involvement in any lysosomal storage disease constitutes the greatest challenge to simple enzyme replacement therapy.

Technology to by pass the BBB appears to be presently emerging. This can be best described as a "Trojan horse approach": one compound, which is recognized by the blood brain barrier (BBB) as "friendly", and is, therefore, allowed to pass through the BBB into the brain (the "Trojan horse") is conjugated or "fused" with the molecule targeted to enter the brain for a therapeutic purpose (Dietz et al, 2004).

The "Trojan horse", then, carries the drug on "its back" into the brain, through the BBB. Large molecules, such as enzymes, which are normally unable to penetrate to the brain, can thus be mounted on ("conjugated to" or "fused with") a molecule, which is BBB-friendly, and deceptively move across the BBB. Hence, fusion proteins comprising BBB targeting antibodies or receptor ligands and recombinant enzymes or other proteins could be potentially utilized to treat neurological disorders of the central nervous system.

Ailments such as Alzheimer's disease and stroke comprise natural targets for the utilization of this strategy.

One model vector used to transport desirable drugs and particularly proteins across the BBB is the murine monoclonal antibody (mAb) against rat transferrin receptor designated as OX26. This approach utilizes the high expression level of transferrin receptors on the brain capillary endothelial cells, which make up of the BBB in vivo. Once the OX26-drug conjugate binds to an epitope on the transferrin receptor, it undergoes receptor-dependent physiologic internalization and transport through the BBB.

There are several examples of successful conjugation of neuroactive or neuroprotective agents to OX26 mAb, allowing access of the desirable molecules into the brain. Perhaps the best example of successful delivery of an enzyme across the blood-brain barrier (BBB) in an experimental setting has been very recently reported. Zhang and Pardridge (2005) conjugated bacterial β-galactosidase to a rat antibody directed towards the transferrin receptor via a streptavidin-biotin linkage, and detected a 10 fold increase in brain uptake of the enzyme following intravenous injection of the enzyme-antibody conjugate, but not of the unconjugated enzyme. Of particular importance was the finding that more than 90% of the enzyme conjugate that entered into the endothelial compartment of the brain passed through the BBB to enter brain parenchyma.

A potential improvement in this approach which utilized mouse monoclonal antibody against rat transferrin receptor, has been recently suggested based on the use of mouse anti-human insulin receptor, which allows a several fold greater BBB permeability in primates, as compared with the brain uptake of the OX26 mAb in rats (Wu, et al., 1997).

Human β-hexosaminidase A α chain is expressed as precursor polypeptide consisting of 529 amino acid residues, set forth in SEQ ID NO:13. A signal peptide consisting of 22 amino acid residues at the amino terminus is cleaved, leaving a 507 amino acid proprotein. The mature peptide consists of amino acids 109-529, set forth in SEQ ID NO:14. A polypeptide comprising amino acids 1-191 of the alpha subunit is set forth in SEQ ID NO:15, A polypeptide comprising amino acids 403-529 of the alpha subunit is set forth in SEQ ID NO:16, The polynucleotide sequence of human β-hexosaminidase A alpha chain (accession number NM_000520) corresponding to SEQ ID NO:13, is set forth in SEQ ID NO:17:

The polynucleotide sequences corresponding to polypeptide sequences set forth in SEQ ID NO:14, SEQ ID NO:15 and SEQ ID NO:16 are set forth in SEQ ID NO:18, SEQ ID NO:19 and SEQ ID NO:20, respectively.

The amino acid sequence of human β-hexosaminidase A beta subunit preproprotein (accession number NP_000512) is set forth in SEQ ID NO:21. The corresponding polynucleotide sequence (accession number NM_000521) is set forth in SEQ ID NO:22

Delivery of Large Proteins to the Brain

Impressive as the results of the leading receptor antibody-based chimeric peptide approach for the introduction of BBB-impermeable agents to the brain may be, there are concerns with regard to the potential immunogenicity of the anti-transferrin or anti-insulin receptor antibody, as well as with their effects on systemic iron or carbohydrate metabolism, respectively. Additionally, the extent of penetration attained by these methods into the brain beyond the immediate post capillary or periventricular zones is an area of uncertainty (Moos and Morgan, 2001).

Hence, an alternative approach proposed in the present project is to utilize native molecules that cross the BBB, such as G-CSF and the hormone leptin as peptide drug delivery vector. Apparently, despite their distinct and dissimilar biological roles, both peptides are capable of crossing the blood brain barrier and bind to receptors which are not only presumed to be expressed on the BBB, but also share common structural motifs. The primary structure of the leptin receptor belongs to the cytokine-class1 family, the single membrane-spanning receptor, and is highly related to the gp130 signal-transducing component of the G-CSF receptor (G-CSFR).

The leptin transport system is a candidate for transporting molecules conjugated to leptin into the brain, a scenario in which leptin may serve as a passive "Trojan horse". In contrast, if a molecule of interest is conjugated to G-CSF, utilizing its ability to cross the BBB, the delivery of G-CSF per se to the brain may exert independent beneficial neuroprotective, antiapoptotic and perhaps neuroregenerative effects. G-CSF was shown to induce neuronal differentiation in vitro and ameliorate long-term cerebral damage after cortical ischemia, to enhance angiogenesis and improve neurological recovery and long-term functional recovery after focal cerebral ischemia, reduce infarct size and inflammatory response following permanent experimentally induced ischemia and induce long-term sensorimotor recovery after intracerebral hemorrhage.

Without wishing to be bound to theory, the G-CSF-HEXA or leptin-HEXA conjugate may serve a dual purpose: breakdown of stored GM2 ganglioside on one hand, thus correcting the major metabolic impairment characteristic of Tay-Sachs disease through the supply of normal HEXA. Additionally, G-CSF-HEXA, can induce nerve cell regeneration and arrest brain cell apoptosis (secondary to GM2-accumulation) through the anti-apoptotic effect of G-CSF per se.

While mature human β-hexosaminidase A is a phosphorylated and glycosylated heterodimer made of alpha and beta chain subunits, each of which is the product of a different gene, either the complete molecule or the alpha chain alone may require transporting through the BBB. The latter appears technically easier, and may indeed be sufficient: one study showed that alpha-chain was taken up by HexA (HEXA)-deficient cells in the culture medium, which was followed by restoration of intracellular HexA activity (Guidotti, ibid)

Pharmacology

The term "pharmaceutical composition" refers to a composition suitable for pharmaceutical use in a subject, including an animal or human. Preferably the subject is a human. A pharmaceutical composition comprises a therapeutically effective amount of the G-CSF chimeric protein or leptin chimeric protein and a pharmaceutically acceptable carrier. In some embodiments a pharmaceutical composition comprises a therapeutically effective amount of a recombinant expression vector encoding a G-CSF fusion protein or leptin fusion protein and a pharmaceutically acceptable carrier.

Accordingly the present invention provides a pharmaceutical composition comprising as an active agent a molecule selected from the group consisting of a) a chimeric protein for the delivery of a therapeutic enzyme across the blood brain barrier, and b) a polynucleotide encoding a chimeric protein for the delivery of a therapeutic enzyme across the blood brain barrier;

wherein the chimeric protein comprises a protein hormone covalently linked to a therapeutic enzyme or active fragment thereof, wherein the protein hormone is able to cross the blood brain barrier; and the therapeutic enzyme is an enzyme whose deficiency is linked to a lysosomal storage disease;
and a pharmaceutically acceptable excipient or carrier.

Herein the term "excipient" or "carrier" refers to an inert substance added to a pharmaceutical composition to further facilitate administration of a compound. Examples, without limitation, of excipients include saline, calcium carbonate, calcium phosphate, various sugars and types of starch, cellulose derivatives, gelatin, vegetable oils and polyethylene glycols. Pharmaceutical compositions may also include one or more additional active ingredients.

Apart from other considerations, the fact that the novel active ingredients of the invention are polypeptides dictates that the formulation be suitable for delivery of these types of compounds. The pharmaceutical composition of this invention may be administered by any suitable means, such as topically, intranasally, subcutaneously, intramuscularly, intravenously, intra-arterially, intraarticularly, intralesionally or parenterally. Ordinarily, intravenous administration is preferred. Continuous intravenous delivery may be preferred via an osmotic pump.

In general, polypeptides are less suitable for oral administration due to susceptibility to digestion by gastric acids or intestinal enzymes, but it is now disclosed that the compositions according to the present invention may be administered orally.

The chimeric proteins of the present invention as active ingredients are dissolved, dispersed or admixed in a diluent or excipient that is pharmaceutically acceptable and compatible with the active ingredient as is well known. Suitable excipients are, for example, water, saline, phosphate buffered saline (PBS), dextrose, glycerol, ethanol, or the like and combinations thereof. Other suitable carriers are well known to those in the art. (See, for example, Ansel et al., 1990 and Gennaro, 1990). In addition, if desired, the composition can contain minor amounts of auxiliary substances such as wetting or emulsifying agents, pH buffering agents.

Pharmaceutical compositions of the present invention may be manufactured by processes well known in the art, e.g., by means of conventional mixing, dissolving, granulating, grinding, pulverizing, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active compounds into preparations which, can be used pharmaceutically. Proper formulation is dependent upon the route of administration chosen.

For injection, the compounds of the invention may be formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants for example, polyethylene glycol, are generally known in the art.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for the chosen route of administration. For buccal administration, the compositions may take the form of tablets or lozenges formulated in conventional manner.

Pharmaceutical compositions for parenteral administration include aqueous solutions of the active ingredients in water-soluble form. Additionally, suspensions of the active compounds may be prepared as appropriate oily injection suspensions. Suitable natural or synthetic carriers are well known in the art (Pillai et al., 2001). Optionally, the suspension may also contain suitable stabilizers or agents, which increase the solubility of the compounds, to allow for the preparation of highly concentrated solutions. Alternatively, the active ingredient may be in powder form for reconstitution with a suitable vehicle, e.g., sterile, pyrogen-free water, before use.

For administration by inhalation, the variants for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in an inhaler or insufflator may be formulated containing a powder mix of the peptide and a suitable powder base such as lactose or starch.

The compounds of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a "therapeutically effective amount" means an amount of a compound effective to prevent, delay, alleviate or ameliorate symptoms of a disease of the subject being treated. Determination of a therapeutically effective amount is well within the capability of those skilled in the art.

Toxicity and therapeutic efficacy of the conjugates described herein can be determined by standard pharmaceutical procedures in cell cultures or experimental animals, e.g., by determining the $IC_{50}$ (the concentration which provides 50% inhibition) and the $LD_{50}$ (lethal dose causing death in 50% of the tested animals) for a subject compound. The data obtained from these cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition (e.g. Fingl, et al., 1975, in "The Pharmacological Basis of Therapeutics", Ch. 1 p. 1).

Depending on the severity and responsiveness of the condition to be treated, dosing can also be a single administration of a slow release composition, with course of treatment lasting from several days to several weeks or until cure is effected or diminution of the disease state is achieved. The amount of a composition to be administered will, of course, be dependent on the subject being treated, the severity of the affliction, the manner of administration, the judgment of the prescribing physician, and all other relevant factors.

The foregoing formulations and administration methods are intended to be illustrative and not limiting. It will be appreciated that, using the teaching provided herein, other suitable formulations and modes of administration can be readily devised.

A tablet may be made by compression or molding, optionally with one or more accessory ingredients. Compressed tablets may be prepared by compressing in a suitable machine the active peptide(s) in a free-flowing form such as a powder or granules, optionally mixed with a binder, (e.g. povidone, gelatin, hydroxypropylmethyl cellulose), lubricant, inert diluent, preservative, disintegrant (e.g. sodium starch glycollate, cross-linked povidone, cross-linked sodium carboxymethyl cellulose), surface active or dispersing agent. Molded tablets may be made by molding in a suitable machine a mixture of the powdered conjugate moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile.

Syrup may be made by adding the conjugate(s) to a concentrated, aqueous solution of a sugar, for example, sucrose, to which may also be added any necessary ingredients. Such accessory ingredients may include flavorings, an agent to retard crystallization of the sugar or an agent to increase the solubility of any other ingredients, such as a polyhydric alcohol, for example, glycerol or sorbitol.

In addition to the aforementioned ingredients, the formulations of this invention may further include one or more accessory ingredient(s) selected from diluents, buffers, flavoring agents, binders, surface active agents, thickeners, lubricants, preservatives, (including antioxidants) and the like.

The following examples are intended to be merely illustrative in nature and to be construed in a non-limitative fashion.

EXAMPLES

The following abbreviations are used in the examples, description and claims.
G-CSF: Granulocyte colony stimulating factor
HEXA: alpha subunit of β-hexosaminidase A
CAT: chloramphenicol-acetyl-transferase
SPDP: cross-linking reagent succinimidyl 3-(–2-pyridyl-dithio)-propionate
LSD: lysosome storage disease
LOTS: Late Onset Tay Sachs Example 1: Outline of Experimental System Objective: To test the delivery of enzymes into the brain by the use of hormone-enzyme conjugates. G-CSF-HEXA conjugates for the treatment of LOTS serves as a test case.

Specific aims: Define an efficient system for the production of a structurally normal human recombinant alpha subunit of β-hexosaminidase A which allows normal β-hexosaminidase A activity or, the for the production of the entire β-hexosaminidase A molecule.

Generation of conjugates of G-CSF-CAT or leptin-CAT (chloramphenicol acetyl-transferase). Examination of the brain activity of CAT following peripheral injection of G-CSF-CAT or leptin-CAT complex in normal mice Generation of a G-CSF-HEXA (or β-hexosaminidase A) conjugate or leptin-HEXA (or β-hexosaminidase A) complex.

Examination of the uptake and effect of added synthetic alpha subunit alone and G-CSF-HEXA (and other) conjugates on β-hexosaminidase activity in white blood cells obtained from LOTS patients.

Delivery of the radio-labeled G-CSF- or leptin-based conjugates carrying HEXA or β-hexosaminidase A to normal mice via peripheral injection, followed by examination of the mouse brain for the presence of the injected β-hexosaminidase A/human alpha chain/human alpha+ mouse beta heterodimer.

Delivery of the G-CSF- or leptin-based conjugates carrying HEXA or β-hexosaminidase A to the Tay Sachs mouse via peripheral injection, followed by examination of the mouse brain for the presence of the injected β-hexosaminidase A/human alpha chain/human alpha-mouse beta heterodimer and for β-hexosaminidase A activity.

Assessment of the effect of long term G-CSF/HEXA conjugates on brain GM2 content in Tay Sachs mice.

Example 2: Expression of G-CSF in Mouse Tissue

FIG. 1 depicts RT-PCR products using primers specific for the mouse G-CSFR. G-CSFR mRNA was detected in aortic homogenates, peritoneal macrophages and brain tissue, with the expected size of 567 basepairs (bp). The lanes of the gel are as follows:

Lane 1: Marker; Lanes 2 and 3: aortic homogenates; Lanes 4 and 5: peritoneal macrophages; Lanes 6 and 7: brain; Lane 8 negative control.

Figure 2:
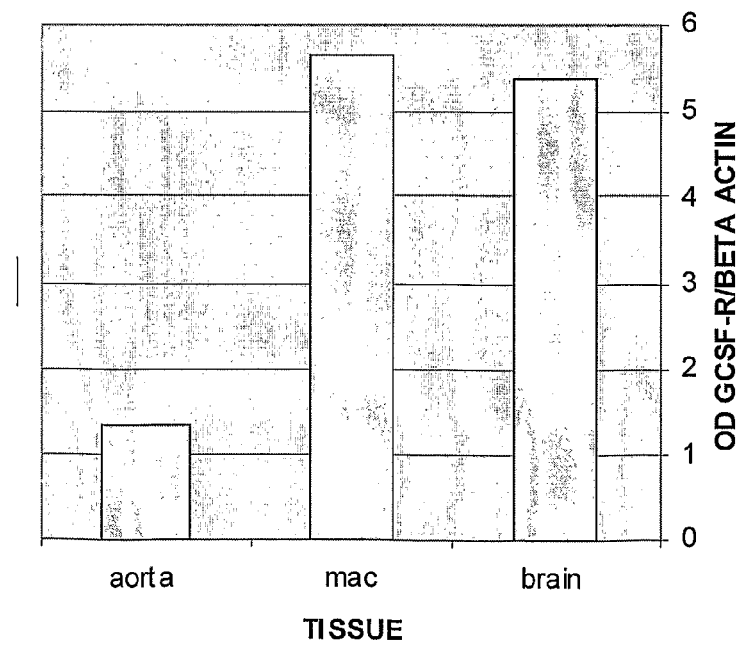
FIG. 2 depicts G-CSFR mRNA expression as measured by optic densitometry (OD) and corrected relative to a control gene.

FIG. 2 depicts G-CSFR mRNA expression as measured by optic densitometry (OD) and corrected relative to the house keeping gene beta actin. As shown, the expression of G-CSFR mRNA relative to beta actin mRNA is as high in brain extracts as in peritoneal macrophages.

Example 3: Biosynthesis of the α Subunit of β-Hexosaminidase (HEXA)

Active HEXA is produced by cloning the HEXA cDNA polynucleotide into an expression vector and expressing the protein in an expression system, e.g. baculoviral vectors in insect cells.

Example 4: Conjugation of HEXA and Chloramphenicol Acetyl Transferase to Hormone a) G-CSF/CAT conjugates: Before testing HEXA, G-CSF and leptin are conjugated to chloramphenicol-acetyl transferase (CAT). The G-CSF-CAT conjugate serves as a means to show that G-CSF-based conjugates are able to cross the BBB, enter the brain tissue and retain activity of the conjugated enzyme.

b) HEXA is conjugated to G-CSF or leptin using different chemical approaches. In order for HEXA to be released from the carrier protein after it enters to the brain (cells) reversible cross-linkers will be used for conjugation. Some of the cross-linkers are based on S—S (disulfide) groups that can be reduced to reduced to an SH group thus releasing the HEXA in the brain.

Another conjugate using the avidin-biotin system as cross-linker, similar to the ones described by (Zhang and Pardridge, 2005) are prepared. Preliminary results have shown that the avidin-biotin complex can dissociate in vivo, thus releasing the HEXA from the other proteins in the target tissue.

Example 5: In Vitro Testing of Conjugates

A clinical testing system in which β-Hexosaminidase A activity is examined in peripheral white blood cells to diagnose Tay Sachs disease is utilized. The clinical assay involves obtaining peripheral white blood cells from Lots patients, culturing the cells and exposing the cells to vehicle or HEXA or G-CSF-HEXA and or leptin-HEXA conjugates.

Example 6: In Vivo Injection G-CSF-CAT and or Leptin-CAT Conjugates in Mice

CAT alone or G-CSF-CAT or Leptin-CAT conjugates are injected to anaesthetized mice intravenously, via the jugular vein. To detect CAT retained in the brain vascular compartment, plasma volume is replaced by slow intra-aortic injection of ice-cold PBS, followed by injection of fixative solution. The brain is removed and prepared for immunohistochemistry using an anti-CAT antibody.

In additional experiments, brain CAT activity is assayed, using tissue homogenates from various parts of the brain, including cortex and cerebellum, comparing mice receiving free CAT or G-CSF-CAT. To remove vascular or capillary components from the assayed homogenates such that only truly neural "parenchymatous" tissue will be assayed, the capillary deletion technique described by Triguero et al., (1999), which essentially precipitates out the capillary components before the performance of the CAT assay, is performed.

Figure 3:
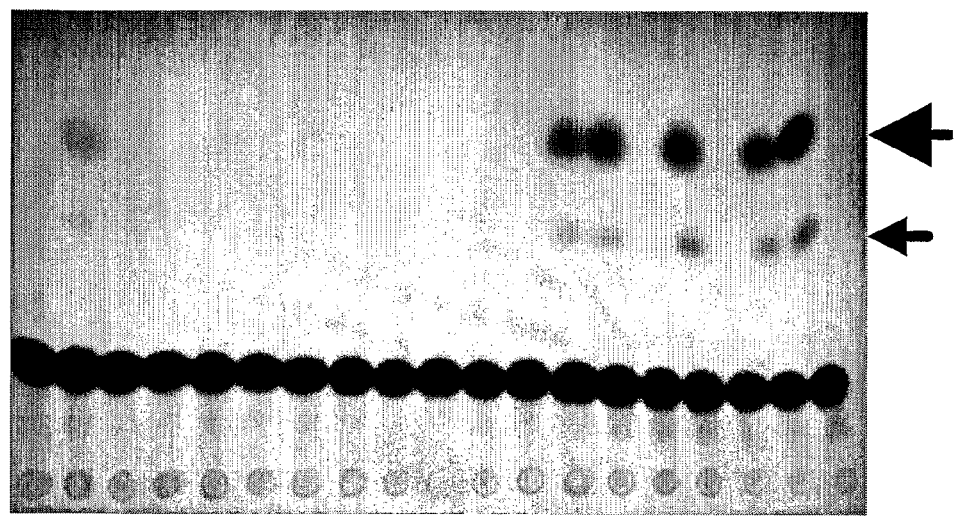
FIG. 3 shows Chloramphenicol (CAT, $C^{14}$) activity in human cell homogenates containing various concentrations of expressed CAT or no active enzyme.

FIG. 3 shows CAT activity detection in human cell homogenates (umbilical cord cells) containing either various concentrations of expressed CAT (shown in the form of monoacetylated Chloramphenicol $C^{14}$, large arrow; deacetylated Chloramphenicol $C^{14}$ small arrow) or no active enzyme.

Example 7: In Vivo Injection of Labeled G-CSF-HEXA and Leptin-HEXA Conjugates

The ability of the HEXA conjugates to cross the BBB is examined in normal mice receiving peripheral injection of the radiolabeled conjugates. Because β-hexosaminidase A is abundantly present in the normal brain, radiolabeled HEXA is followed.

Experimental Plan:
a) $^{125}I$ radiolabeling of HEXA prior to conjugation.
b) Conjugation of G-CSF or leptin to radiolabeled HEXA.
c) Injection of labeled and unlabeled free HEXA and G-CSF-HEXA leptin-HEXA conjugates to mice intravenously using the same technique described above.
d) Preparation of the brain slices for autoradiography to detect the presence and localization of labeled enzyme in the brain.

Example 8: In Vivo Injection of G-CSF-HEXA or Leptin-HEXA Conjugates in a Tay Sachs Mouse Model While original reports of the generation of a β-hexosaminidase A alpha subunit (HEXA) knockout mouse ("Tay Sachs mouse") suggested that this mutation resulted in a neurologically normal phenotype expressing only some minor and inconsequential changes in the brain, more recent observations over the entire life span of the mouse indicated that it comprises an informative model for human late onset Tay Sachs disease (Yamanaka, et al., 1994). As in the human disease, the knock-out mice are HEXA deficient, but appear entirely normal until their adulthood (age of 12 months), at which time they gradually develop signs reminiscent of the late onset, chronic form of human disease: limb spasticity, weight loss, tremors, abnormal posture with lordosis, possible visual impairment, and, late in the disease, muscle weakness, clasping of the limbs, and myoclonic twitches of the head (Miklyaeva, et al., 2004). Of note is the finding that progression of the neurological deficit is slow and parallels the increasing storage of GM2 ganglioside.

Experimental Plan:
1) Genotyping is performed by PCR using genomic DNA extracted from tails and specific primers.
2) Protocols for injection of G-CSF-HEXA and unconjugated HEXA and preparation of brain tissue for the measurement of enzyme activity are as described infra.
3) β-hexosaminidase activity is assessed separately for HEXA and HEXB, using substrates recognized by the alpha (HEXA) or beta (HEXB) subunit of the enzyme. Dosing is determined empirically.

Example 9: Long Term Delivery of G-CSF-HEXA

G-CSF-HEXA is shown to increase brain HEXA activity in Tay Sachs mice, therefore chronic treatment should result in reduced accumulation of GM2 in the brain.

Experimental Plan:
G-CSF-HEXA conjugate is delivered through osmotic mini-pumps (Alzet®) implanted under the skin or repeated daily to weekly intraperitoneal injections. Calculated initial dose is double of that found effective in intravenous acute delivery experiments. Blood HEXA is determined to see that proper increase in circulating HEXA has been achieved through the infusion pump system or the intraperitoneal injections. Comparisons between brain histology, immunohistochemistry for HEXA and GM2, HEXA/beta hexosaminidase activities between and GM2 content in HEXA−/− mice receiving G-CSF/HEXA conjugate, HEXA alone or placebo are made.

Figure 4:
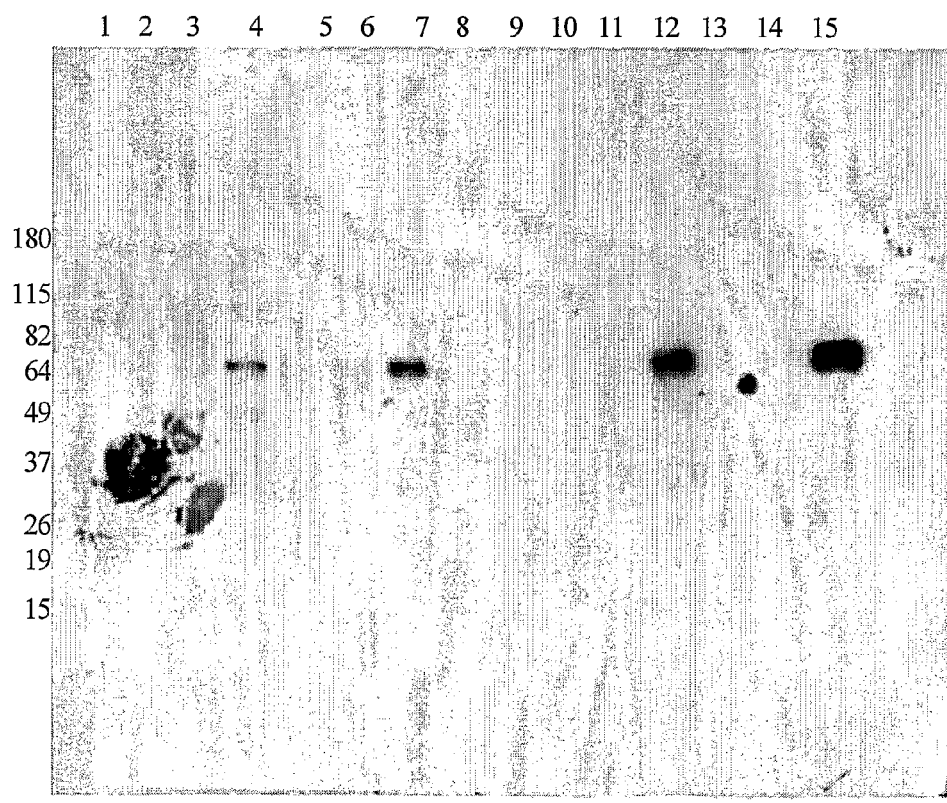
FIG. 4 presents Western analysis of expressed HEXA protein, using an anti-poly-HIS antibody. Note the 64 kD bands corresponding to the expected HEXA.

Example 10: Preparatory Steps Towards the Biosynthesis of Hexa and Initial Biosynthesis of HEXA Species HEXA cDNA was first sub-cloned and re-sequenced to exclude potential deleterious mutations prior to the production of the HEXA polypeptide. A HIS-fusion construct (cleavable HIS tag) of the alpha subunit was then generated and the gene was cloned into a baculovirus expression vector; followed by screening (through restriction digest analysis) of the new constructs; sequence analysis of the selected clone and finally, expression of the vector in insect cells. The resultant soluble (SOL) and insoluble (INSOL) protein expression was estimated using SDS PAGE (Coomassie stained) and Western Blot analysis for protein expression, with antibodies directed against the HIS-tag (FIG. 4). Table 2 provides a brief description of the samples loaded in the wells.

TABLE 2

| Lane | Sample description |
|------|-------------------|
| 1 | MARKER |
| 2 | 0 Hr SOL 0.3% |
| 3 | 24 Hr SOL 0.3% |
| 4 | 48 Hr SOL 0.3% |
| 5 | 0 Hr SOL 3.0% |
| 6 | 24 Hr SOL 3.0% |
| 7 | 48 Hr SOL 3.0% |
| 8 | SPACE |
| 9 | MARKER |
| 10 | 0 Hr INSOL 0.3% |
| 11 | 24 Hr INSOL 0.3% |
| 12 | 48 Hr INSOL 0.3% |
| 13 | 0 Hr INSOL 3.0% |
| 14 | 24 Hr INSOL 3.0% |
| 15 | 48 Hr INSOL 3.0% |

The expected 64 kD bands corresponding to the HIS-tagged HEXA can be seen. To explore the best purification method for this protein, two separate expression experiments were used, one of which was treated with urea and the other with NP40 detergent at time of lysis. Each was then run on a Ni-NTA column. Half of each pooled sample was dialyzed to remove the imidazole. The results of urea-treated samples are not shown. Total protein yield following this initial purification was 2.2-2.57 mg/ml.

Example 11: Preparation of "Model" G-CSF-Based Conjugates: G-CSF/Chloramphenicol Acetyl Transferase Conjugate and G-CSF/Beta Galactosidase Conjugate To test the feasibility of G-CSF-based conjugation strategy, a G-CSF conjugate with Chloramphenicol Acetyl Transferase (CAT) was generated. This "model conjugate" was a means to assess the possibility that G-CSF-based conjugates can cross the BBB, such that CAT, a 25 kD protein (which usually functions only as a 75 kD trimer) can be subsequently detected in the target tissue, specifically brain tissue.

For the conjugation procedure, the SPDP reagent having two reactive groups; NHS ester, which is reactive towards amino residues, and pyridyldithiol, which reacts with sulfhydryl groups, was used. Protein modification was done by adding SPDP in excess (5 fold) to G-CSF or to CAT. Excess SPDP was removed by gel filtration (Sephadex G-25 equilibrated with buffer phosphate PH 7.2 0.008% Tween 80) for G-CSF and by dialysis with buffer phosphate (PH 7.2) for CAT. At the second step, the SPDP-G-CSF mixture was reduced with DTT and excess DTT was removed by gel filtration. The G-CSF-containing SH group was then combined with CAT-SPDP at a molar ratio of 1:1. The conjugation mixture was incubated for 1 h at room temperature, and stored at −20° C.

The presence of both G-GSF and CAT in the conjugate was confirmed by immunoprecipitation with a G-CSF antibody followed by western blotting of the immunopurified product with an anti-CAT antibody.

Example 12: Detection of CAT Within the Mouse Brain Following Peripheral (Intravenous) Injection of G-CSF/CAT Conjugate Evidence that G-CSF can transport the bacterial CAT enzyme into the mouse brain is shown in FIGS. 6-7. Mice were anaesthetized and the jugular vein was cannulated. The G-CSF/CAT conjugate, (60 μg of G-CSF at the pre-conjugation phase/100 gr BW) was injected via the jugular vein as a bolus of 100 μL. Two hours later, a needle was inserted into the left ventricle and a catheter was placed to drain the right atrium. To remove the entire blood volume containing the injected conjugate, PBS solution was infused into the left ventricle (total of ~15-20 ml) and blood was drained through the right atrial catheter until the effluent was entirely clear of blood. Brain tissue was collected from various areas.

Tissue was homogenized and extracted for Western blotting using a monoclonal anti-CAT antibody (ab5410, Abcam). Western blots from the cerebellum (left panel) and olfactory bulb (right panel) from a control (Con) mouse receiving vehicle only and from two mice receiving G-CSF/CAT conjugate (R1, R2) are shown in FIG. 5. The CAT bands found in brain homogenates are marked by arrows. The difference between control and treated mice as quantified by optical densitometry is indicated "Optical 1 v1" in arbitrary relative units.

FIGS. 6 and 7 depict detection of CAT in the mouse brain following peripheral intravenous injection of the G-CSF/CAT conjugate by an immunofluorescence study using anti-CAT antibodies. FIG. 6A-6C depict immunofluorescence detection of CAT in the mouse brain, following peripheral injection of a G-CSF/CAT conjugate, using anti-CAT antibodies (Sigma 1:2000 dilution) as the primary antibody and FITC-goat anti-rabbit IgG (H+L) conjugate as the secondary antibody at a dilution of 1:100. Brain slices (15 uM; cryosection) from control (6 Å) and G-CSF/CAT conjugate-treated mice (6B and 6C)) are shown, and staining represents CAT within the brain.

Figure 7A:
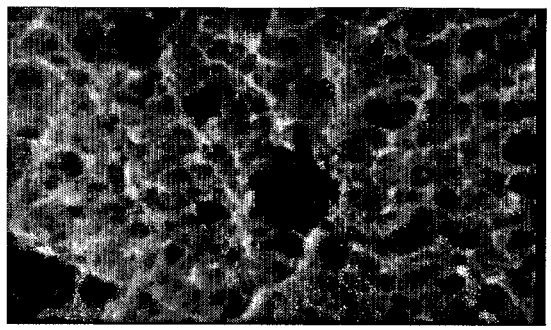
FIG. 7A-7C depicts immunofluorescence detection of CAT in the mouse brain, following peripheral injection of a G-CSF/CAT conjugate.
Figure 7B:
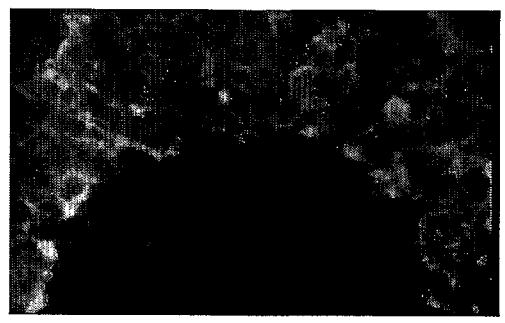
Figure 7C:
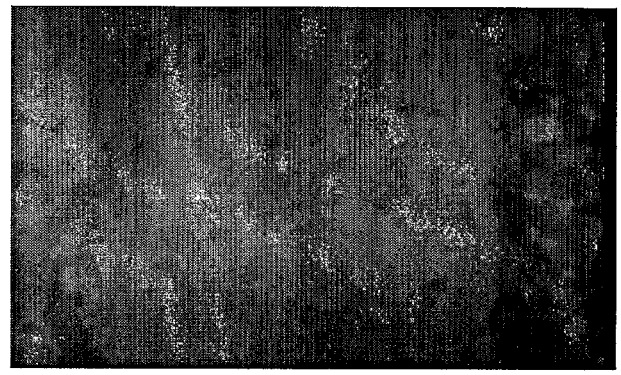

FIG. 7A, represents untreated mouse brain, FIG. 7B the represents mouse brain following IV injection of a CAT-GCSF conjugate (×10 magnification) and FIG. 7C represents an enlarged segment of the sample presented in the 7B (×40 magnification).

Figure 8A:
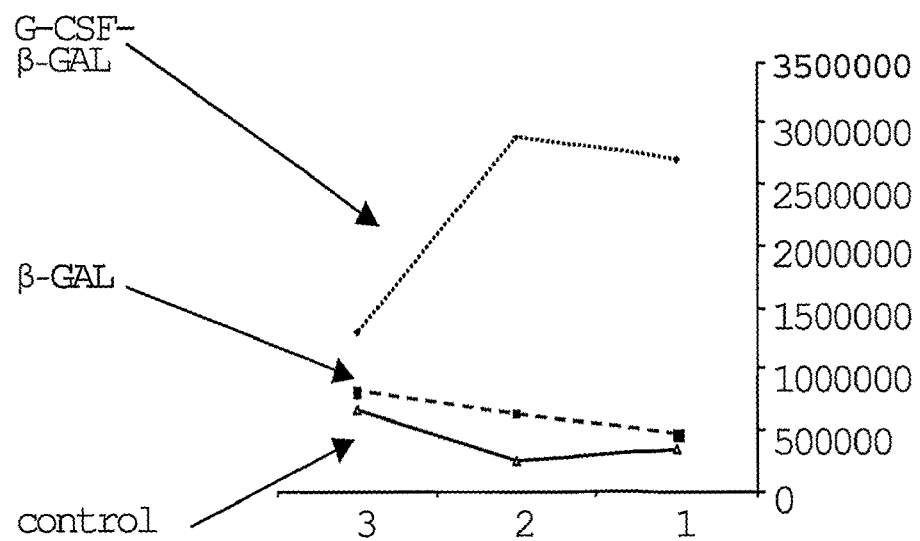
FIG. 8A-8B illustrates β-galactosidase (β-gal) activity in the cerebral cortex (8A) and cerebellum (8B) of mice injected intravenously with vehicle (control-triangles), (β-gal alone (squares) and G-CSF/β-gal conjugate (diamonds). Method of injection was performed as described in the Examples section for the G-CSF/CAT conjugate.
Figure 8B:
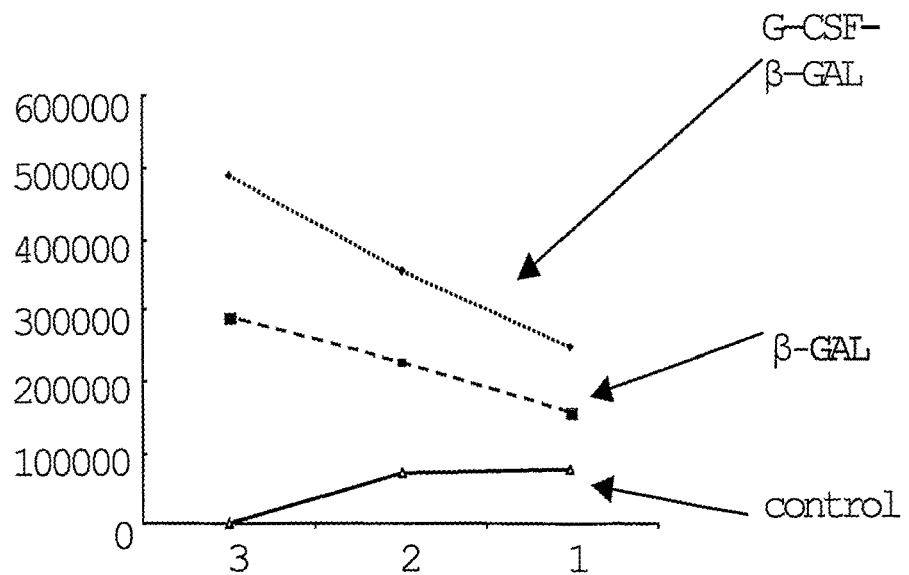

Example 13: Preparation of G-CSF/β-Galactosidase Conjugate (G-CSF/β-gal) and Detection of Increased Brain β Galactosidase Activity in the Mice Injected with the G-CSF/β-Gal Conjugate A G-CSF/β-gal conjugate was prepared based on the same principles described for the G-CSF/CAT conjugate. FIGS. 8A and 8B show β-gal activity in the brain following peripheral injection of conjugated and unconjugated enzyme. The brain tissue was extracted with Promega lysis buffer, followed by homogenization. The homogenate was centrifuged for 10 min at 12,000 g, and the supernatant was used to measure (3-galactosidase activity with the Promega Beta-Glo® assay kit a method used to quantitate β-galactosidase activity by addition of reagent consisting of the enzyme substrate and providing a bright luminescent signal light units that can be measured with a luminometer. Relative light emitted measured was normalized to the protein content in the organ extract measured by the BCA. The results provide further evidence for the ability of G-CSF to serve as a transport for large proteins, in this case β-gal (MW~116 kD). The dotted lines represent the activity of the G-CSF-β-gal conjugate; the dashed line represents β-gal; the solid lines represent the negative control levels.

While certain embodiments of the invention have been illustrated and described, it will be clear that the invention is not limited to the embodiments described herein. Numerous modifications, changes, variations, substitutions and equivalents will be apparent to those skilled in the art

REFERENCES

Akli, S., Guidotti, J. E., Vigne, E., Perricaudet, M., Sandhoff, K., Kahn, A., Poenaru, L. Restoration of hexosaminidase A activity in human Tay-Sachs fibroblasts via adenoviral vector-mediated gene transfer. Gene Ther. 1996; 3:769-774.

Brady, R. O., Schiffmann, R., Enzyme-replacement therapy for metabolic storage disorders. Lancet Neurol. 2004; 3:752-756.

Burguera, B., Couce, M. E., Long, J., Lamsam, J., Jensen, M. D., Parisi, J. E., Lloyd, R. V. The long form of the leptin receptor (OB-Rb) is widely expressed in the human brain. Neuroendocrinology, 2000; 61:187-195.

Conzelmann, E., Sandhoff, K. Partial enzyme deficiencies: residual activities and the development of neurological disorders. Dev Neurosci. 1983; 84; 6:58-71.

Creighton, T. E. (1984) Protein: Structures and Molecular Properties, pp. 55-60, W.H. Freeman and Co. New York, N.Y.

Dietz, G. P., Bahr, M. Delivery of bioactive molecules into the cell: the Trojan horse approach. Mol Cell Neurosci. 2004; 27:85-131

Guidotti, J., Akli, S., Castelnau-Ptakhine, L., Kahn, A., Poenaru, L. "Retrovirus-mediated enzymatic correction of Tay-Sachs defect in transduced and non-transduced cells." Hum Mol. Genet. 1998; 7:831-838.

Lacorazza, H. D., Flax, J. D., Snyder E. Y., Jendoubi, M. Expression of human beta-hexosaminidase alpha-subunit gene (the gene defect of Tay-Sachs disease) in mouse brains upon engraftment of transduced progenitor cells. Nat. Med. 1996; 2:424-429.

Mahuran, D. J. The biochemistry of HEXA and HEXB gene mutations causing GM2 gangliosidosis. Biochim Biophys Acta. 1991; 22; 1096:87-94.

Mahuran, D. J. Biochemical consequences of mutations causing the GM2 gangliosidoses. Biochim Biophys Acta. 1999; 1455:105-138.

Miklyaeva, E. I., Dong, W., Bureau, A., Fattahie, R, Xu, Y., Su, M., Fick, G. H., Huang, J. Q., Igdoura, S., Hanai, N., Gravel, R. A. Late onset Tay-Sachs disease in mice with targeted disruption of the Hexa gene: behavioral changes and pathology of the central nervous system. Brain Res. 2004; 19; 1001:37-50.

Moos, T., Morgan, E. H.: Restricted transport of anti-transferrin receptor antibody (OX26) through the blood-brain barrier in the rat. J. Neurochem. 2001; 79:119-129.

Myerowitz, R., Piekarz, R., Neufeld, E. F., Shows, T. B., Suzuki. K. Human beta-hexosaminidase alpha chain: coding sequence and homology with the beta chain. PNAS USA. 1985; 82:7830-7834.

Navon, R. Late-onset GM2 gangliosidosis and other hexosaminidase mutations among Jews. Adv Genet. 2001; 44:185-197.

Neudorfer, O., Pastores, G. M., Zeng, B. J., Gianutsos, J., Zaroff, C. M., Kolodny, E. H. Late-onset Tay-Sachs disease: phenotypic characterization and genotypic correlations in 21 affected patients. Genet Med. 2005; 7:119-123. Pan et al "Efficient transfer of receptor-associated protein (RAP) across the blood-brain barrier", J Cell Sci. 117(Pt 21): 5071-8, 2004)

Paulson, O. B. and Newman, E. A. Does the release of potassium from astrocyte endfeet regulate cerebral blood flow?Science. 1987; 237: 896-898.

Pardridge, W. M. Molecular biology of the blood-brain barrier. Mol Biotechnol. 2005; 30(1): 57-70.

Pennybacker. M., Liessem, B., Moczall, H., Tifft C. J., Sandhoff, K., Proia, R. L. Identification of domains in human beta-hexosaminidase that determine substrate specificity. J Biol. Chem. 1996; 271:17377-17382.

Pillai et al., Polymers in drug delivery. Curr. Opin. Chem. Biol. 2001; 5:447.

Sambrook et al., Molecular Cloning: A Laboratory Manual, Cold Springs Harbor Laboratory, New York, 1992.

Schabitz, W. R. et al. Neuroprotective effect of granulocyte colony-stimulating factor after focal cerebral ischemia. Stroke. 2003; 34:745-751.

Wu, D., Yang, J., Pardridge, W. M. Drug targeting of a peptide radiopharmaceutical through the primary blood-brain barrier in vivo with a monoclonal antibody to the human insulin receptor. J Clin Invest. 1997100: 1804-1812.

Yamanaka, S, Johnson, M. D., Grinberg, A., Westphal, H., Crawley, J. N., Taniike, M., Suzuki, K., Proia, R. L. Targeted disruption of the Hexa gene results in mice with biochemical and pathologic features of Tay-Sachs disease. PNAS USA 1994; 91, 9975-9979.

Zhang, Y., Pardridge, W. M. Delivery of beta-galactosidase to mouse brain via the blood-brain barrier transferrin receptor. J Pharmacol Exp Ther. 2005; 313:1075-81.

While the present invention has been described with reference to the specific embodiments thereof it should be understood by those skilled in the art that various changes may be made and equivalents may be substituted without departing from the spirit and scope of the present invention as described by the claims, which follow.

The invention claimed is:

1. A chimeric protein for the delivery of a therapeutic enzyme across the blood brain barrier, the chimeric protein comprising a protein hormone which is granulocyte colony stimulating factor (G-CSF) or a precursor or an active fragment thereof having an the amino acid sequence as set forth in any one of SEQ ID NOSs: 5-6 and 9-10,
covalently linked to a therapeutic enzyme which is β-hexosaminidase A (HEXA) or a precursor or active fragment thereof, having the amino acid sequence as set forth in any one of SEQ ID NOS: 13-16, wherein the G-CSF is able to cross the blood brain barrier; and wherein β-hexosaminidase A is an enzyme whose deficiency is linked to GM2-gangliosidosis type I/Tay-Sachs disease.

2. The chimeric protein according to claim 1, which comprises an amino acid sequence set forth in any one of SEQ ID NOS: 23-25.

3. The chimeric protein according to claim 1, wherein said protein hormone and said therapeutic enzyme or fragment thereof are covalently linked by a linking molecule.

4. The chimeric protein according to claim 3, wherein said linking molecule comprises a disulfide bond.

5. A pharmaceutical composition comprising as an active agent a chimeric protein according to claim 1 and a pharmaceutically acceptable excipient or carrier.

6. The pharmaceutical composition according to claim 5, wherein the composition is formulated for administration in a form selected from the group consisting of topical, intranasal, subcutaneous, intramuscular, intravenous, intra-arterial, intraarticular, intralesional and parenteral.

7. The pharmaceutical composition according to claim 6 formulated for intravenous delivery.

8. The pharmaceutical composition according to claim 6 formulated for continuous delivery via an osmotic pump.

9. The chimeric protein according to claim 1 capable of passing through the blood-brain barrier and entering a lysosome of a cell within the central nervous system.

10. The chimeric protein according to claim 1, wherein Tay-Sachs is Late Onset Tay-Sachs disease (LOTS).

11. A method of treating a lysosomal storage disease in a subject in need thereof comprising administering to the subject a pharmaceutical composition according to claim 5.

12. A method of effecting neural regeneration in a subject in need thereof comprising administering to the subject a pharmaceutical composition according to claim 5.

13. The method according to claim 11, wherein said subject is a human.

14. The method according to claim 11, wherein the lysosomal storage disease is Tay-Sachs disease.

15. The method according to claim 12 wherein the pharmaceutical composition is administered to a subject that has Tay-Sachs disease.

16. The method according to claim 11, wherein said subject is a human.

* * * * *